US012781168B2

(12) United States Patent
Chua et al.

(10) Patent No.: US 12,781,168 B2
(45) Date of Patent: Nov. 3, 2026

(54) INTEGRATED SYSTEM FOR MULTIPLE CULTIVATIONS OF A BIOLOGICAL AGENT AND METHODS OF USE THEREOF

(71) Applicants: The Hong Kong Polytechnic University, Hong Kong (CN); City University of Hong Kong, Hong Kong (CN)

(72) Inventors: Song Lin Chua, Hong Kong (CN); Yeping Ma, Hong Kong (CN); Bee Luan Khoo, Singapore (SG)

(73) Assignees: The Hong Kong Polytechnic University, Hong Kong (CN); City University of Hong Kong, Hong Kong (CN)

( * ) Notice: Subject to any disclaimer, the term of this patent is extended or adjusted under 35 U.S.C. 154(b) by 434 days.

(21) Appl. No.: 18/486,269

(22) Filed: Oct. 13, 2023

(65) Prior Publication Data

US 2025/0122455 A1 Apr. 17, 2025

(51) Int. Cl.
*C12M 3/06* (2006.01)
*B01L 3/00* (2006.01)
*C12Q 1/18* (2006.01)

(52) U.S. Cl.
CPC ....... *C12M 23/16* (2013.01); *B01L 3/502707* (2013.01); *B01L 3/502738* (2013.01);
(Continued)

(58) Field of Classification Search
CPC .............. C12M 23/16; B01L 3/502707; B01L 3/502738; B01L 2200/025;
(Continued)

(56) References Cited

U.S. PATENT DOCUMENTS

2022/0113300 A1* 4/2022 Khoo .................... C12M 23/16

OTHER PUBLICATIONS

Ma, Y. P. et al.; Distinct bacterial population dynamics and disease dissemination after biofilm dispersal and disassembly; The ISME Journal, vol. 17, Jun. 3, 2023, pp. 1290-1302.

(Continued)

*Primary Examiner* — David W Berke-Schlessel
*Assistant Examiner* — Trent R Clarke
(74) *Attorney, Agent, or Firm* — S&F/WEHRW

(57) ABSTRACT

The present invention provides an integrated system built on a microfluidics with multiple layers including a cell culture surface and different chambers configured to allow multiple cultivations of a biological agent, formation of three-dimensional multicellular culture model or biofilm, colonization and re-colonization of the biological agent responsive to a stimuli introduced to the integrated system. Such stimuli include physical, chemical and/or biological substance that may affect proliferation, differentiation, and/or function of the biological agent. The biological agent includes a biofilm-forming microbe such as a ubiquitous biofilm-forming bacterial species or biological cells or tissues of a different origin or species such as eukaryotic cells/tissues. The present integrated system can be used in drug screening, establishment of disease model in vitro or in vivo, evaluation of an anti-microbial efficacy, and studying cell-cell interaction.

20 Claims, 34 Drawing Sheets

(52) U.S. Cl.
CPC .......... *C12Q 1/18* (2013.01); *B01L 2200/025* (2013.01); *B01L 2200/0694* (2013.01); *B01L 2200/12* (2013.01); *B01L 2300/0867* (2013.01); *B01L 2300/12* (2013.01)

(58) Field of Classification Search
CPC ......... B01L 2200/0694; B01L 2200/12; B01L 2300/0867; B01L 2300/12; C12Q 1/18
See application file for complete search history.

(56) References Cited

OTHER PUBLICATIONS

Barraud N, Hassett DJ, Hwang SH, Rice SA, Kjelleberg S, Webb JS. Involvement of nitric oxide in biofilm dispersal of Pseudomonas aeruginosa. J Bacteriol. 2006; 188(21):7344-53.
Chambers JR, Cherny KE, Sauer K. Susceptibility of Pseudomonas aeruginosa Dispersed Cells to Antimicrobial Agents Is Dependent on the Dispersion Cue and Class of the Antimicrobial Agent Used. Antimicrobial Agents and Chemotherapy. 2017;61(12):e00846-17.
Christensen LD, Gennip Mv, Rybtke MT, Wu H, Chiang W-C, Alhede M, et al. Clearance of Pseudomonas aeruginosa Foreign-Body Biofilm Infections through Reduction of the Cyclic Di-GMP Level in the Bacteria. Infection and Immunity. 2013;81(8):2705-13.
Chua SL, Liu Y, Yam JK, Chen Y, Vejborg RM, Tan BG, et al. Dispersed cells represent a distinct stage in the transition from bacterial biofilm to planktonic lifestyles. Nat Commun. 2014;5:4462.
Chua SL, Ding Y, Liu Y, Cai Z, Zhou J, Swarup S, et al. Reactive oxygen species drive evolution of pro-biofilm variants in pathogens by modulating cyclic-di-GMP levels. Open Biology. 2016;6(11):160162.
Fleming D, Rumbaugh K. The Consequences of Biofilm Dispersal on the Host. Scientific Reports. 2018;8(1):10738.
França a, Pérez-Cabezas B, Correia A, Pier GB, Cerca N, Vilanova M. *Staphylococcus epidermidis* Biofilm-Released Cells Induce a Prompt and More Marked In vivo Inflammatory-Type Response than Planktonic or Biofilm Cells. Frontiers in Microbiology. 2016; 7:1530.
Guzmán-Soto I, McTiernan C, Gonzalez-Gomez M, Ross A, Gupta K, Suuronen EJ, et al. Mimicking biofilm formation and development: Recent progress in in vitro and in vivo biofilm models. iScience. 2021;24(5):102443.
Guilhen C, Charbonnel N, Parisot N, Gueguen N, Iltis A, Forestier C, et al. Transcriptional profiling of Klebsiella pneumoniae defines signatures for planktonic, sessile and biofilm-dispersed cells. BMC Genomics. 2016;17(1):237.
Guilhen C, Forestier C, Balestrino D. Biofilm dispersal: multiple elaborate strategies for dissemination of bacteria with unique properties. Molecular microbiology. 2017; 105(2):188-210.
Hay AJ, Zhu J, Camilli A. Host Intestinal Signal-Promoted Biofilm Dispersal Induces Vibrio cholerae Colonization. Infection and Immunity. 2015;83(1):317-23.
Li Y, Petrova OE, Su S, Lau GW, Panmanee W, Na R, et al. BdIA, DipA and Induced Dispersion Contribute to Acute Virulence and Chronic Persistence of Pseudomonas aeruginosa. PLOS Pathogens. 2014; 10(6):e1004168.
Rumbaugh KP, Sauer K. Biofilm dispersion. Nature Reviews Microbiology. 2020; 18(10):571-86.
Sternberg C, Tolker-Nielsen T. Growing and analyzing biofilms in flow cells. Curr Protoc Microbiol. 2006; Chapter 1:Unit 1B.2.
Uppuluri P, Zaldívar MA, Anderson MZ, Dunn MJ, Berman J, Ribot JLL, et al. Candida albicans Dispersed Cells Are Developmentally Distinct from Biofilm and Planktonic Cells. mBio. 2018;9(4):e01338-18.
Yu M, Chua SL. Demolishing the great wall of biofilms in Gram-negative bacteria: To disrupt or disperse? Medicinal Research Reviews. 2020;40(3):1103-16.

* cited by examiner

INTEGRATED SYSTEM FOR MULTIPLE CULTIVATIONS OF A BIOLOGICAL AGENT AND METHODS OF USE THEREOF

TECHNICAL FIELD

The present invention relates to an integrated system, in particular, a microfluidic-based system configured to cultivate a biological agent on a cell culture surface in a chamber, form a three-dimensional culture model, and facilitate subsequent spread to a fresh cell culture surface in a separate chamber for evaluating growth, maturation and dissemination of the biological agent responsive to stimuli introduced to the integrated system.

BACKGROUND

The following references are cited and discussed hereinafter:

1. Barraud N, Hassett D J, Hwang S H, Rice S A, Kjelleberg S, Webb J S. Involvement of nitric oxide in biofilm dispersal of *Pseudomonas aeruginosa*. J Bacteriol. 2006; 188(21):7344-53;
2. Chambers J R, Cherny K E, Sauer K. Susceptibility of *Pseudomonas aeruginosa* Dispersed Cells to Antimicrobial Agents Is Dependent on the Dispersion Cue and Class of the Antimicrobial Agent Used. Antimicrobial Agents and Chemotherapy. 2017; 61(12):e00846-17;
3. Christensen L D, Gennip Mv, Rybtke M T, Wu H, Chiang W-C, Alhede M, et al. Clearance of *Pseudomonas aeruginosa* Foreign-Body Biofilm Infections through Reduction of the Cyclic Di-GMP Level in the Bacteria. Infection and Immunity. 2013; 81(8):2705-13;
4. Chua S L, Liu Y, Yam J K, Chen Y, Vejborg R M, Tan B G, et al. Dispersed cells represent a distinct stage in the transition from bacterial biofilm to planktonic lifestyles. Nat Commun. 2014; 5:4462;
5. Chua S L, Ding Y, Liu Y, Cai Z, Zhou J, Swarup S, et al. Reactive oxygen species drive evolution of pro-biofilm variants in pathogens by modulating cyclic-di-GMP levels. Open Biology. 2016; 6(11):160162;
6. Fleming D, Rumbaugh K. The Consequences of Biofilm Dispersal on the Host. Scientific Reports. 2018; 8(1): 10738;
7. Franga A, Pérez-Cabezas B, Correia A, Pier G B, Cerca N, Vilanova M. *Staphylococcus epidermidis* Biofilm-Released Cells Induce a Prompt and More Marked In vivo Inflammatory-Type Response than Planktonic or Biofilm Cells. Frontiers in Microbiology. 2016; 7:1530;
8. Guzmán-Soto I, McTiernan C, Gonzalez-Gomez M, Ross A, Gupta K, Suuronen E J, et al. Mimicking biofilm formation and development: Recent progress in in vitro and in vivo biofilm models. iScience. 2021; 24(5): 102443;
9. Guilhen C, Charbonnel N, Parisot N, Gueguen N, Iltis A, Forestier C, et al. Transcriptional profiling of *Klebsiella pneumoniae* defines signatures for planktonic, sessile and biofilm-dispersed cells. BMC Genomics. 2016; 17(1): 237;
10. Guilhen C, Forestier C, Balestrino D. Biofilm dispersal: multiple elaborate strategies for dissemination of bacteria with unique properties. Molecular microbiology. 2017; 105(2):188-210;
11. Hay A J, Zhu J, Camilli A. Host Intestinal Signal-Promoted Biofilm Dispersal Induces *Vibrio cholerae* Colonization. Infection and Immunity. 2015; 83(1):317-23;
12. Li Y, Petrova O E, Su S, Lau G W, Panmanee W, Na R, et al. BdlA, DipA and Induced Dispersion Contribute to Acute Virulence and Chronic Persistence of *Pseudomonas aeruginosa*. PLOS Pathogens. 2014; 10(6):e1004168;
13. Rumbaugh K P, Sauer K. Biofilm dispersion. Nature Reviews Microbiology. 2020; 18(10):571-86;
14. Sternberg C, Tolker-Nielsen T. Growing and analyzing biofilms in flow cells. Curr Protoc Microbiol. 2006; Chapter 1: Unit 1B.2;
15. Uppuluri P, Zaldivar M A, Anderson M Z, Dunn M J, Berman J, Ribot J L L, et al. *Candida albicans* Dispersed Cells Are Developmentally Distinct from Biofilm and Planktonic Cells. mBio. 2018; 9(4):e01338-18;
16. Yu M, Chua S L. Demolishing the great wall of biofilms in Gram-negative bacteria: To disrupt or disperse?Medicinal Research Reviews. 2020; 40(3):1103-16.

Biofilms are multicellular communities of prokaryotic and/or eukaryotic origin that may attach to a surface or aggregate in suspension. In general, they bind onto a surface and start to form biofilms which mature over time. Biofilm dispersal occurs when organisms depart from the biofilm, migrate and recolonize new areas to ensure species' survival. Although biofilms are highly common in the environment and complex organisms (e.g., animals and plants), they are involved in biofouling and corrosion of manmade structures and difficult-to-treat antibiotic-resistant infections in human organ systems. Hence, it is important to study biofilms and develop anti-biofilm strategies to eliminate biofilms. However, biofilms are tedious and slow to cultivate in the laboratory for study.

Current technologies to cultivate microbial biofilms range from growing in static cultures (with limited nutrients) on glass slides, Petri dishes, microwells, and pegs, to continuous flow cultures (constant replenishment of fresh media and removal of waste media), e.g., flow chamber devices (Sternberg and Nielsen, 2006). However, those biofilms were grown on 2D flat surfaces, which resulted in slow growth and morphologies that do not recapitulate those found in in vivo conditions (Guzmán-Soto et al., 2021). Stovar Flow cell developed by Stovar Life Science, Inc can allow cultivation of biological agents on flat surface, so it may partially address the problem, but it lacks the ability to study the dissemination of biological agents. Furthermore, current biofilm cultivation techniques do not consider biofilms' dispersal and recolonization processes, despite various studies showing that biofilm dispersal is a unique process in the biofilm life cycle (Guilhen et al., 2016; Uppuluri et al., 2018; Hay and Camilli, 2015; Chambers et al., 2017; Franga et al., 2016). Advances in microfluidics enable better control and precision of miniaturized biofilm growth at a lower cost than conventional biofilm cultivation means. Different cell model and even animal model can be incorporated into microfluidic-based platform, providing flexibility of evaluating bacterial virulence.

Improving biofilm cultivation techniques will improve the study of biofilm physiology and the development of anti-biofilm agents. The anti-biofilm agents are primarily aimed at dispersing biofilms to release single cells susceptible to and easily eliminated by predators/immune cells, antimicrobials, or other physical means (Rumbaugh and Sauer, 2020). However, current biofilm cultivation techniques are not well-designed to study the biofilm-released bacteria and evaluate the efficacy of antibiofilm agents, resulting in the prolonged collection of biofilm-released bacteria and indirect measurement approaches.

In summary, at least the following drawbacks/problems exist in the prior arts:

No culture device enables convenient study and observation of the spread of biological agents from the initial site of culture to the fresh site;

Slow growth of biological agents;

Overuse plastic culture dishes/flasks to culture biological agents and transfer to new containments.

Therefore, there is an unmet need for a platform to at least mitigate or eliminate the drawbacks or problems in the prior arts.

SUMMARY OF INVENTION

Accordingly, a first aspect of the present invention provides an integrated, microfluidic-based platform catering the entire biofilm life cycle from biofilm formation, dispersal, and recolonization, using some bacterial biofilms as an in vitro model according to certain embodiments and examples described hereinafter.

The microfluidic-based platform in the first aspect is a microfluidic device comprising at least two layers, wherein a first layer of the microfluidic device is connected to a second layer, which allows an introduction of fluids containing biological agents, such as prokaryotic and eukaryotic cells/tissues of the lab, environment and/or clinical origin, to develop into a culture model, and an introduction of chemical agents, such as antimicrobials, antibiotics, anti-pathogenic agents, biofilm dispersal agents, and anti-cancer drugs, or any combination thereof, with a concentration gradient for high throughput screening in parallel.

Exemplarily, the first layer of the at least two layers comprises an array of microwells for three-dimensional (3D) cultivation of microbes with relevance to in vivo settings, whereas microbial cultivation has been conducted on flat 2D surfaces till date. The microfluidic device also comprises a continuous flow setting that enables a consistent replenishment of fresh media into microbial culture and transfer of disseminated biological agent from a first chamber to a second chamber. The microfluidic device further comprises a gradient generator that enables the introduction of more than two compounds or biological agents into the microfluidic device simultaneously after mixing.

In certain embodiments, the microwells are tapered microwells.

In certain embodiments, each of the microwells has a dimension of 150×250×150 μm (length×width×depth).

In certain embodiments, the first layer comprises a cell culture surface comprising a plurality of micropores on an interior surface of the microwells configured to confine biological agents for forming a complex three-dimensional culture model.

In certain embodiments, the biological agents comprise prokaryotic and eukaryotic cells/tissues.

In certain embodiments, the cell culture surface is modified to enable efficient binding of hard-to-bind biological agents, where the surface modification comprises coating a layer of material to facilitate binding of the biological agents.

In certain embodiments, the second layer comprises a plurality of fluid channels each comprising:

a first chamber for colonization and cultivation of a biological agent to form the complex three-dimensional culture model in a first plurality of microwells;

a second chamber for capturing the biological agent disseminated from the complex three-dimensional culture model in the first chamber and re-cultivating thereof in a second plurality of microwells for subsequent analyses.

In certain embodiments, the first chamber is arranged upstream to the second chamber and communicated with each other through a channel in which the fluid communication between the first chamber and the second chamber is controlled by a valve.

In certain embodiments, each of the first and second chambers has a channel depth of about 6 mm.

In certain embodiments, the complex three-dimensional culture model comprises mammalian cell spheroids such as tumor spheroids and microbial biofilms such as bacterial biofilms.

In certain embodiments, the bacterial biofilms comprise bacterial biofilms formed by *Pseudomonas aeruginosa* or any mutant thereof.

In certain embodiments, the microfluidic device further comprises a third layer as the gradient generator and a top layer as a barrier for retaining fluids.

In certain embodiments, the gradient generator has at least two fluid inlets and at least eight output channels, and is arranged upstream to the first chamber of the second layer.

In certain embodiments, the second layer has at least eight fluid inlets to receive fluid output from the output channels of the gradient generator.

In certain embodiments, the microfluidic device is made of polydimethylsiloxane.

In a second aspect, there is provided a method of fabricating the integrated system described in the first aspect comprising providing the three different layers of the microfluidic devices for forming an array of microwells on the first layer, two separate chambers including the primary and secondary chambers for primary and second cultivations of the biological agent and their fluid channels on the second layer in separation by the valve, and the gradient generator configured in a tree-like structure with at least two fluid inlets and a plurality of outlets in the third layer, and then aligning and bonding the first layer, the second layer and the third layer in an order from the bottom to the top of the integrated system. Additionally, a top layer to retain the fluid is included in the microfluidic device.

In a third aspect, there is provided a method for cultivating a biological model, comprising:

(a) establishing a prokaryotic model in the first plurality of microwells in the first chamber of the microfluidic device described in the first aspect to represent microbial colonization and formation of multicellular communities or biofilms, followed by dissemination of the biofilms into biological agents to the second plurality of microwells in the second chamber for recolonization and growth; and (b) providing cell culture conditions that allow concurrent proliferation and interaction of cells based on confined 3D structures.

In certain embodiments, the fluid channel between the first and the second chambers during the formation of the multicellular communities or biofilms is blocked by the valve until the prokaryotic model is established.

In a third aspect, there is provided a method for evaluating efficacy of an agent, wherein said agent affects the proliferation, differentiation, or function of a biological agent. The method comprises:

(i) providing the first chamber of the microfluidic device according to the first aspect described herein with the biological agent;

(ii) contacting the biological agent with the cell culture surface of the microfluidic device;

(iii) providing culture conditions that maintain proliferation and viability of the biological agent to establish a 3D culture model;

(iv) contacting said agent with the 3D culture model in the first chamber; and (v) monitoring the activity of said agent with respect to attachment, colonization, proliferation, survival, and dissemination of the biological agent from the 3D culture model in the first chamber to the second chamber of the microfluidic device.

In certain embodiments, said agent can be initially introduced to the gradient generator of the microfluidic device to establish a concentration gradient before introduced to the first chamber.

In a fourth aspect, there is provided a method for characterizing a test agent, comprising:

(1) providing a biological agent to the first chamber of the microfluidic device according to the first aspect described herein;

(2) contacting the biological agent with the cell culture surface of the microfluidic device;

(3) providing culture conditions that maintain proliferation and viability of the biological agent to establish a confined 3D multicellular structure or biofilm;

(4) contacting the test agent with the 3D multicellular structure or biofilm; and (5) analyzing changes in the biological agent in terms of expression of gene, transcript, or protein levels, genetic markers, stains and dyes, and also biological structures, morphologies, and dynamics thereof.

In certain embodiments, said biological agent expresses a protein or genetic marker important in formation, maturation, and dispersal of multicellular structures or biofilms.

In certain embodiments, said biological agent could be detected by stains and dyes such as crystal violet, Congo red, and other markers such as extracellular components (polysaccharides, proteins/amyloids, or extracellular DNA).

In certain embodiments, the test agent can be a chemical or biological agent.

Other aspects of the present invention include providing a method for studying cell-cell interaction between two different species or types of biological cells/tissues comprising using the integrated system described in the first aspect for contacting the two different species or types of cells or tissues and observing/analyzing any cellular, molecular, genetic, morphological, behavioral and/or dynamic changes in a 3D multicellular structure or biofilm formed by one of the biological cells or tissues. The present invention can also be used as a cell culture vessel or chamber for cultivation and re-cultivation of biological agent into a 3D multicellular culture model, and studying development of certain biological system.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which:

FIG. 12A-12H show that bacterial cells released by CID and EDA possessed differing physiologies, in which: FIG. 12A shows brightfield, fluorescence, and merged images that biofilm dispersed WT/$p_{cdrA}$-gfp cells downregulated GFP expression, while biofilm-disassembled cells retained GFP expression. Representative images are shown, where the scale bar is 10 μm; FIG. 12B shows relative GFP intensity of WT/$p_{cdrA}$-gfp cells after CID or EDA; FIG. 12C shows that ELISA revealed reduced c-di-GMP levels in biofilm dispersed cells and high c-di-GMP levels in biofilm-disassembled cells, where means and s.d. from triplicate experiments are shown; * p<0.001; FIG. 12D shows no biofilm dispersal in ΔbdlA mutant; FIG. 12E shows an effective biofilm disassembly in ΔbdlA mutant; FIG. 12F shows no biofilm dispersal in ΔfliM mutant FIG. 12G shows an effective biofilm disassembly in ΔfliM mutant; FIG. 12**H shows representative fluorescence images that biofilm-dispersed cells primarily existed as single cells, while biofilm-disassembled cells existed as small multicellular aggregates, where the scale bar is 10 μm.

(FIG. 18A), CF173 (FIG. 18B) and CF273 (FIG. 18C) which were dispersed or disassembled by NO (CID) or pectinase (EDA) (middle and lower rows in each cluster of fluorescence images) and recolonized over time (2 hrs).

Skilled artisans will appreciate that elements in the figures are illustrated for simplicity and clarity and have not necessarily been depicted to scale.

DETAILED DESCRIPTION OF THE INVENTION

It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

Described hereinafter are non-limiting examples to facilitate understanding and enablement of the present invention. Scope of the invention should be defined in the appended claims.

Examples

Figure 3:
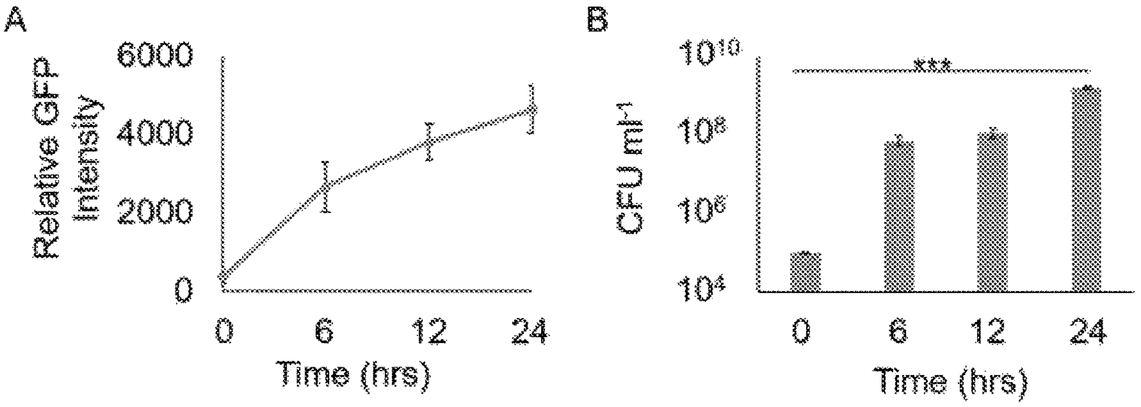
FIG. 3 shows biofilm formation over 24 hrs: (A) Fluorescent intensity of gfp-tagged biofilms; (B) Bacterial cell number in biofilms over time, where the means and s.d. from triplicate experiments were shown; ***$P<0.001$.

Establishment of the "Bio Lm Disperse-then-Recolonize" (BDR) Microfluidic Device Existing bacterial models, such as the flow chamber and Calgary biofilm assay, do not fully recapitulate the 3D structure of biofilms found in vivo (Roberts et al, 2015), and cannot examine dispersion and recolonization in a single device. To overcome these limitations, the "biofilm disperse-then-recolonize" (BDR) microfluidic device 100 (FIG. 1A) was provided to evaluate both biofilm dispersal and recolonization. The BDR microfluidic device 100 comprised three layers (101, 102, 103), where the second layer 102 has a first chamber 104 (or "primary chamber" used herein interchangeably) for initial biofilm formation dispersion, and a second chamber 105 (or "secondary chamber" used herein interchangeably) for capturing biofilm-released cells from the primary chamber 105 for recolonization under continuous flow (FIG. 1B). Each channel contained up to 300 tapered microwells 107 at the first layer 101, compared to flat surfaces commonly used in conventional biofilm cultures, which enabled bacteria such as *P. aeruginosa* to rapidly colonize and form biofilms within 12 hrs under continuous flow as 3D cultures (FIG. 1C, FIG. 3).

In certain embodiments, each of the tapered microwells has a dimension of 150×250×150 μm (length×width×depth), which is different from that of the larger microwells from microplates. These tapered microwells in microfluidic devices are typically used for establishment of 3D cultures, which recapitulates the physiology and behavior of cells in humans. To facilitate formation of biofilm, the interior surface of the tapered microwells has a lot of micropores. The interior surface may be further modified by a coating or subject to plasma treatment to enhance the binding of biofilm to the microwells.

Figure 1A:
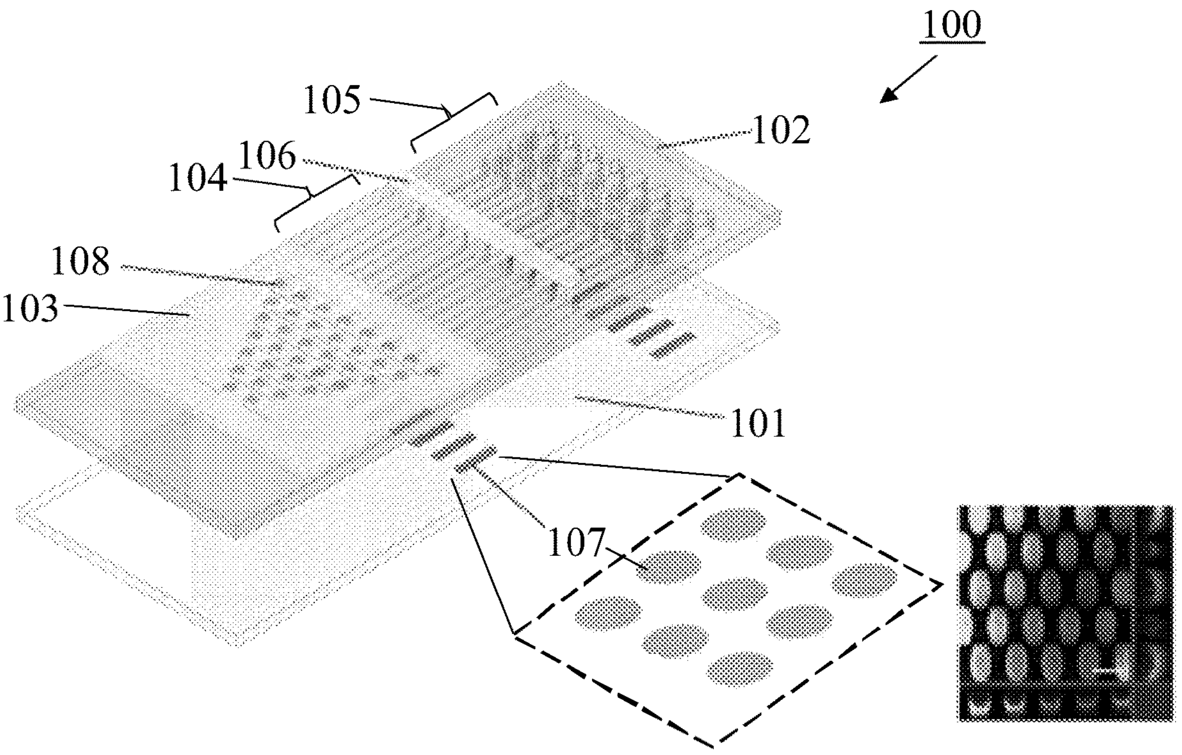
FIG. 1A schematically depicts a structure of a "biofilm-disperse-then-recolonize" (BDR) microfluidic device according to certain embodiments, where the schematic in the inset and fluorescence image on the right panel show some microwells of one chamber and fluorescence signals from the culture model formed in the chamber.
Figure 1B:
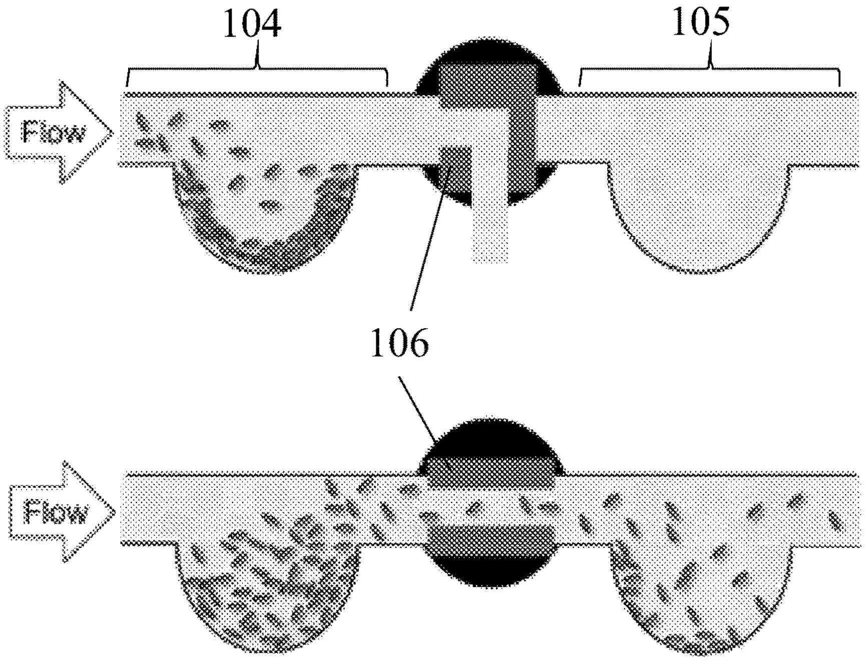
FIG. 1B schematically depicts how biofilm is formed in a first chamber, followed by biofilm dispersal and subsequent recolonization in a second chamber of the BDR microfluidic device.
Figure 1C:
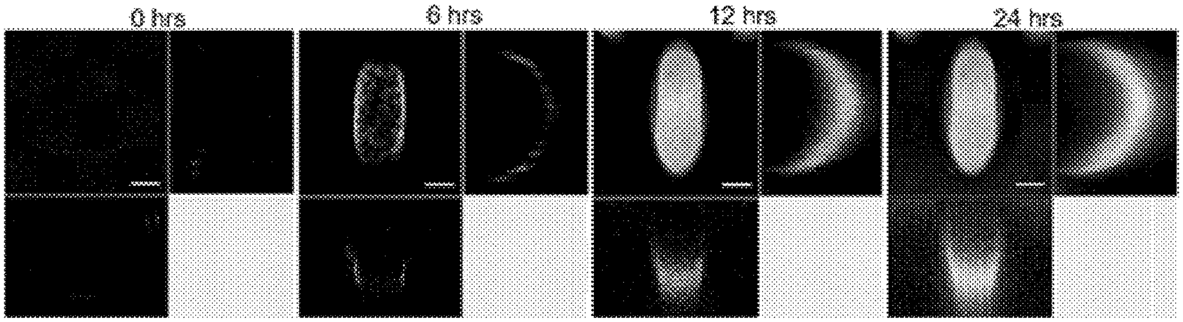
FIG. 1C shows representative fluorescence images of gfp-tagged wild-type (WT) *Pseudomonas aeruginosa* biofilm formation over 24 hrs, where the scale bar is 50 μm.
Figure 4:
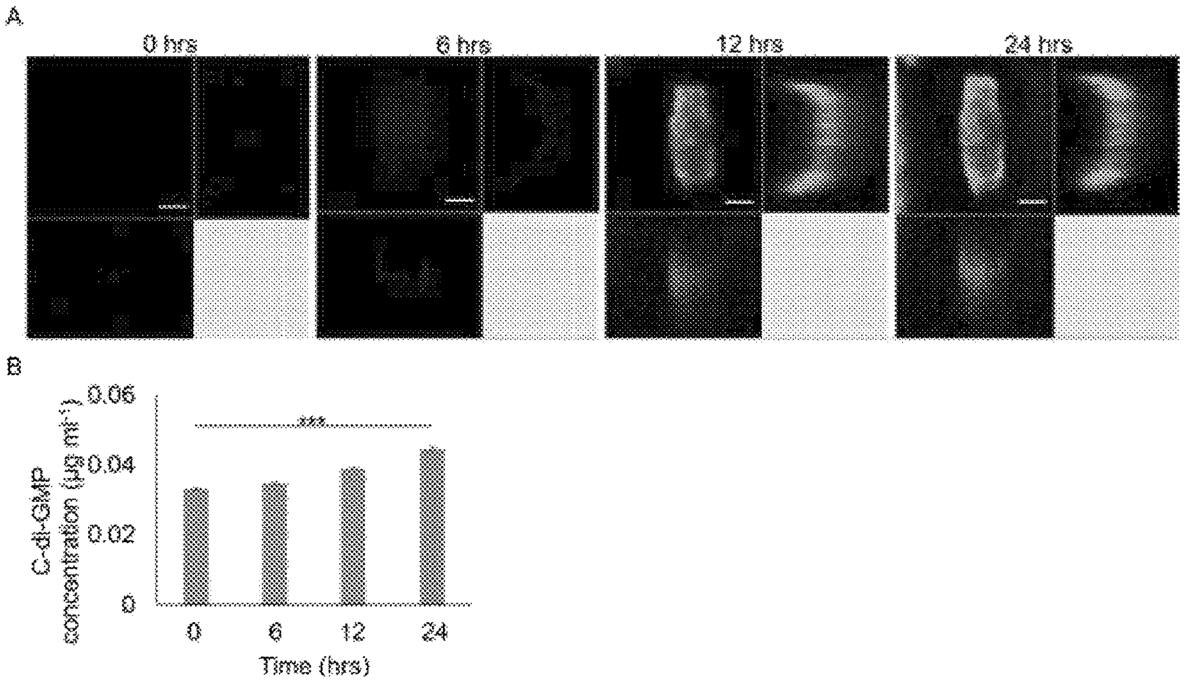
FIG. 4 shows that biofilm biomarkers are expressed in biofilms over 24 hrs: (A) Upregulation of GFP expression by WT/$p_{cdrA}$-gfp; (B) Higher c-di-GMP levels in biofilms, as quantified by ELISA, where the means and s.d. from triplicate experiments were shown; ***$P<0.001$.

A large number of microwells in each channel also provided simultaneous observation of multiple technical replicate wells, enabling reproducibility of the observation (FIG. 1A). FIG. 4 shows that the bacterial communities cultivated in each microwell are true biofilms, as they possessed increased expression of biofilm markers ($p_{cdrA}$-gfp biosensor and c-di-GMP) in bacterial cells. Hence, both biofilm markers indicated that the microwells can be used to cultivate 3D biofilms in BDR device which have similar physiology as a typical biofilm cultivated in vitro or in vivo.

Figure 1D:
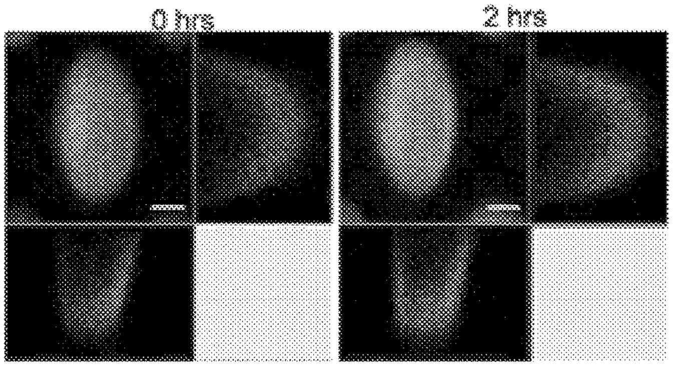
FIG. 1D shows fluorescence images of physiological biofilm dispersal over 2 hrs.
Figure 1E:
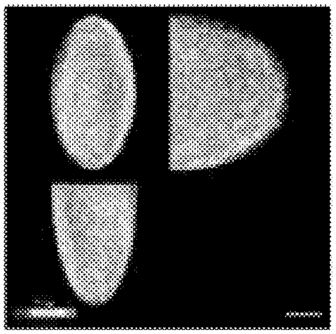
FIG. 1E shows time-resolved cell trajectories of bacteria released from biofilm under physiological conditions, where color scheme from purple to red indicates chronological order from 0 hours to 2 hrs.
Figure 1F:
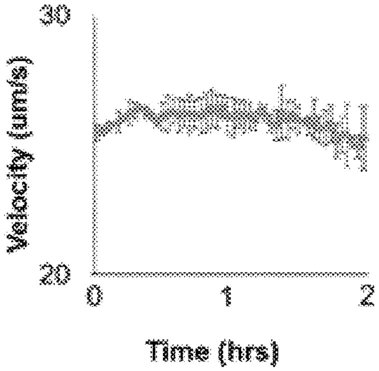
FIG. 1F shows an average velocity of biofilm dispersed cells.

After biofilm cultivation in the primary chamber 105 for 12 hrs, the dispersion process and the performance of the secondary chamber 105 in capturing biofilm-released cells were evaluated by turning on the valve 106 that enables media flow from the primary chamber 104 into the secondary chamber 105. Under normal conditions where media flowed without antibiofilm treatment, the biofilms remained intact after 2 hrs, while basal levels of biofilm dispersal occurred continuously (FIG. 1D). Freshly dispersed cells would enter the media space of the microwell for microscopic observation and eventually exit the microwell (FIG. 1E). The tapered microwells provided sufficient confined boundaries to retain newly dispersed cells for observation, allowing long-term monitoring of cell velocity immediately after dispersion (FIG. 1F). As seen from FIG. 1F, it shows bacterial velocities immediately after dispersion, where the average velocity of bacteria released from biofilm in general remained consistent over time with a value of approximately 30 $\mu m\ s^{-1}$. Although this corroborated with the flagellar-dependent velocities of planktonic bacteria, the objective of this study was to demonstrate a general trend of how bacteria departed from the biofilm over time, instead of tracking individual bacteria due to limitations of the confocal microscopy in capturing 3D images.

Figure 1G:
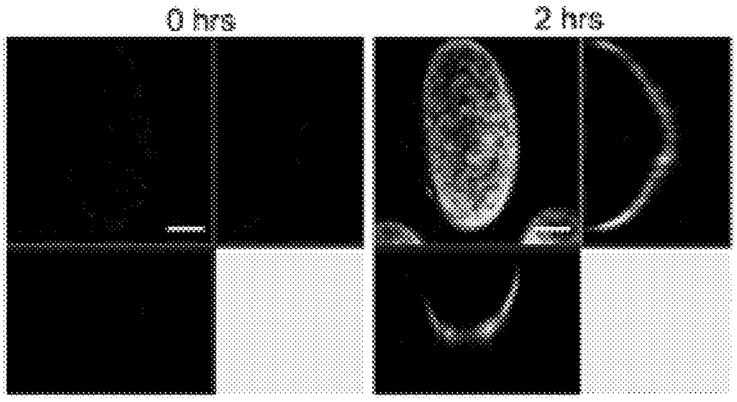
FIG. 1G shows fluorescence images of colonized biofilm-released cells in recolonization chamber over 2 hrs.
Figure 1H:
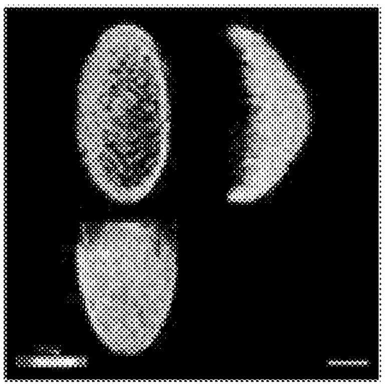
FIG. 1H shows time-resolved cell trajectories of physiologically biofilm dispersed cells upon recolonization, where color scheme from purple to red indicates chronological order from 0 hours to 2 hrs.
Figure 1I:
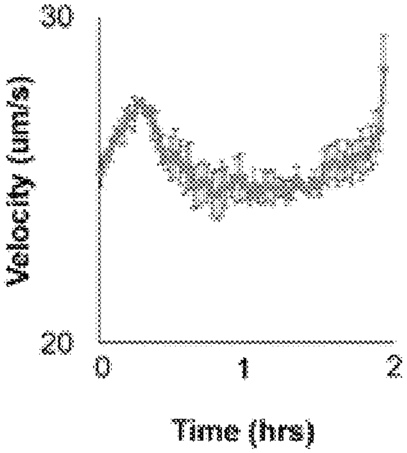
FIG. 1I shows an average velocity of biofilm dispersed cells upon recolonization under physiological conditions.

To recolonize bacterial cells released from biofilms in the primary chamber, the bacterial suspension was allowed to flow from the primary chamber into the secondary chamber, where the microwells in the secondary (recolonization) chamber could capture biofilm-dispersed cells for recolonization (FIG. 1G). Time-resolved cell trajectories revealed the consistent recolonization of dispersed cells (FIG. 1H), which maintained consistent velocities when they were freshly dispersed from the biofilm (FIG. 1I).

Figure 2A:
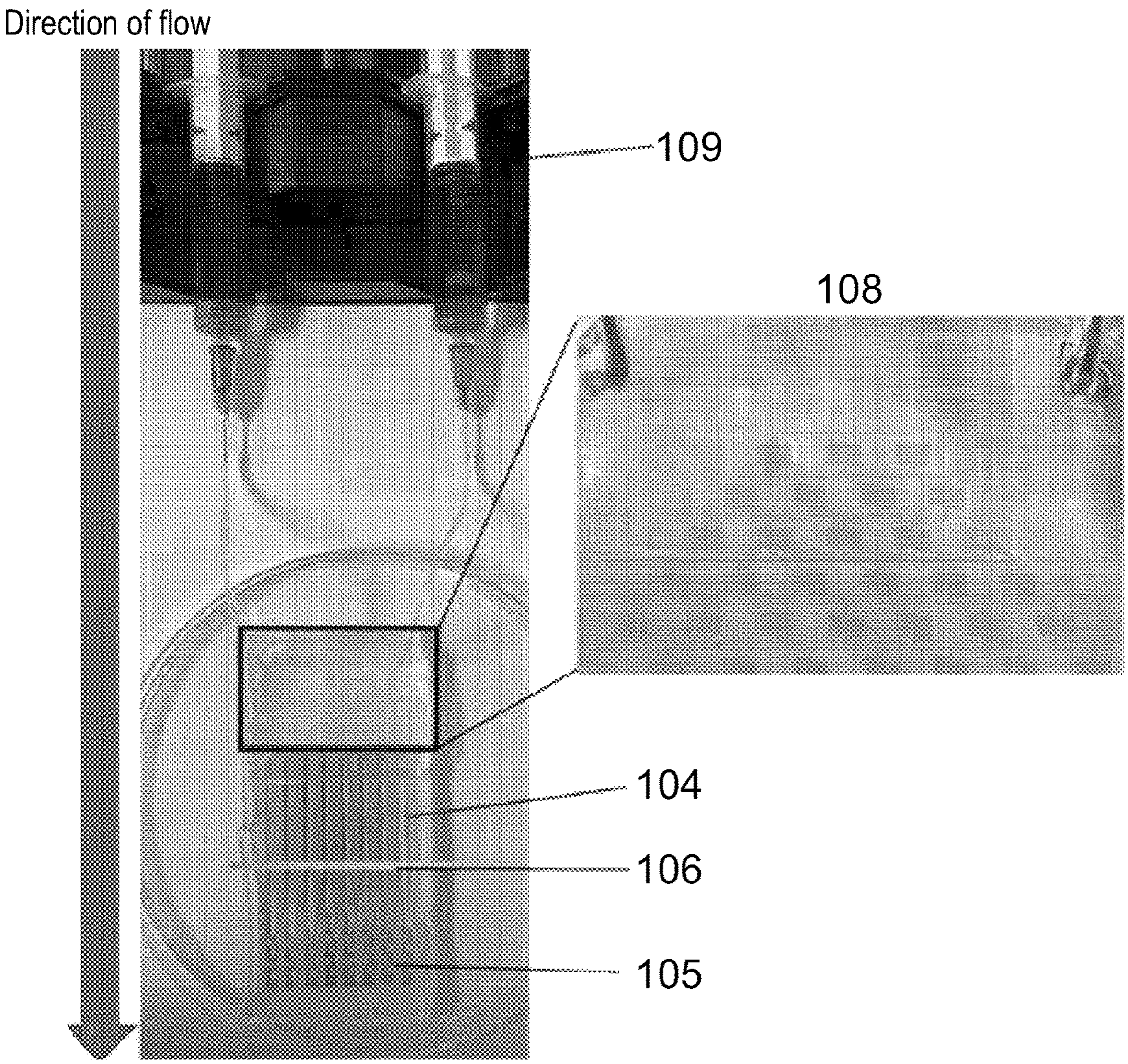
FIG. 2A shows an image from a top view of the BDR microfluidic device according to certain embodiments and a magnified view of a gradient generator thereof.
Figure 2B:
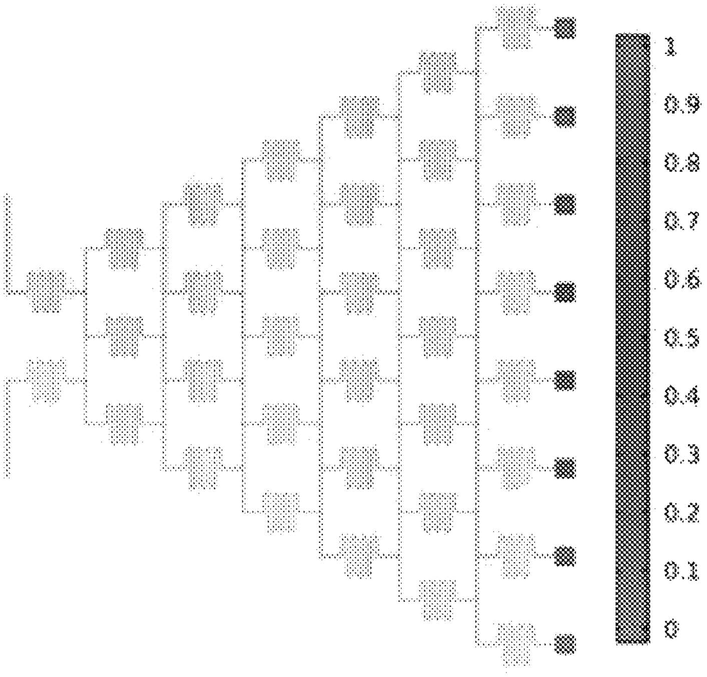
FIG. 2B shows a flow simulation for the gradient generator using COMSOL, where the flow rate is color-coded on the right legend.
Figure 2C:
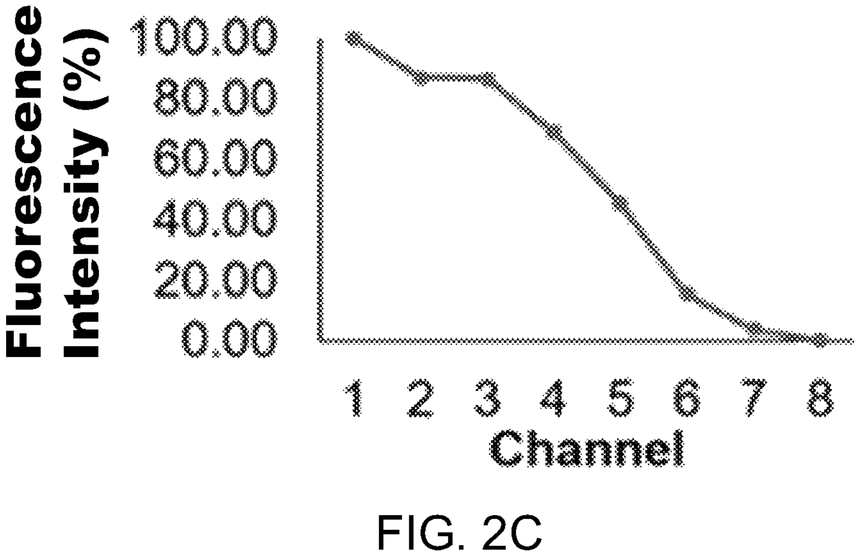
FIG. 2C shows fluorescence dye intensities of 8 channels in the concentration gradient generator.

FIG. 2A shows a prototype of the BDR microfluidic device from a top view, in which the top layer is a gradient generator 108 with two inlets connected to two corresponding syringe pumps 109 for introducing test fluids into the microfluidic device. In the inset, it shows that two different test fluids (the one containing fluorescence dye was in red color) were mixed in different ratio (or concentrations) in each channel (total of eight output channels in this prototype) according to the gradient level of the gradient generator. The second layer under the top layer received the output fluid from the eight output channels of the gradient generator 108, flowed into the first chamber 104 and then second chamber 105 through a fluid channel controlled by a valve 106. As seen from FIG. 2A, the different color tones present in different channels of the first and second chambers represented different concentrations of fluorescence dye flowing through the chambers. FIG. 2B simulated the flow rate of the fluorescence dye in each gradient level of the gradient generator by COMSOL, where the flow rate is shown on the right legend. The red color on the color-code bar represents the highest flow rate of the fluorescence dye, whereas the blue color represents the lowest flow rate thereof. The change in fluorescence dye across the eight output channels is shown in FIG. 2C.

CID Induces Rapid Release of Bacterial Cells

Bacterial cells released from biofilms under physiological conditions can comprise mixed populations of actively dispersed cells departing on their own and passively dispersed cells released from biofilms. Passive dispersal can occur due to biofilm matrix degradation or shear stress. Hence, the next objective was to generate homogenous populations of biofilm-dispersed cells and biofilm-disassembled cells for subsequent analyses.

Figure 5:
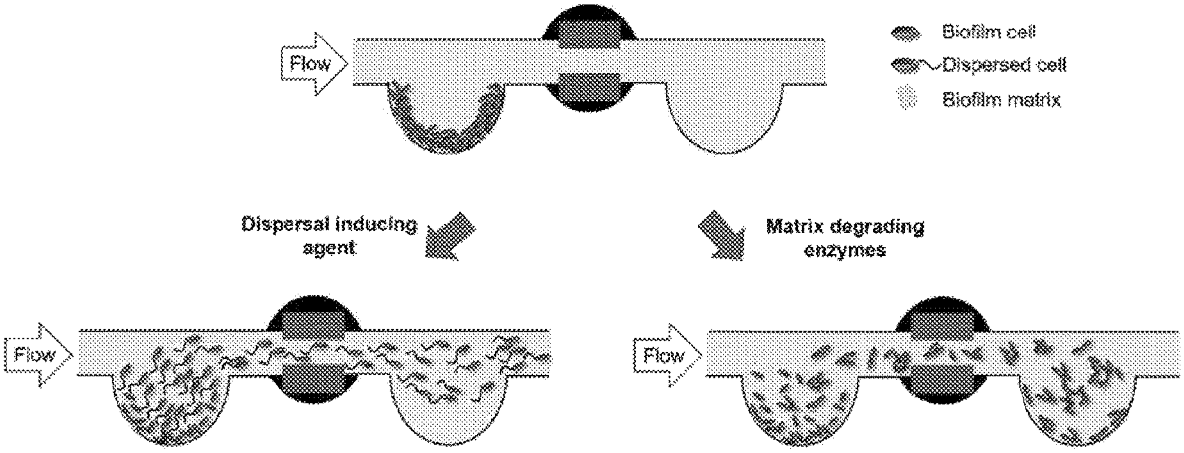
FIG. 5 schematically depicts the differences in biological agent between biofilm chemical-induced dispersal (CID) and biofilm enzymatic disassembly (EDA) in the first and second chambers of the BDR microfluidic device according to certain embodiments.

To study the dynamics of these two modes and their implications in disease dissemination, two anti-biofilm strategies, namely (1) induced biofilm dispersal and (2) biofilm disassembly, were employed. A schematic diagram showing the differences between these two anti-biofilm strategies is depicted in FIG. 5.

Figure 6:
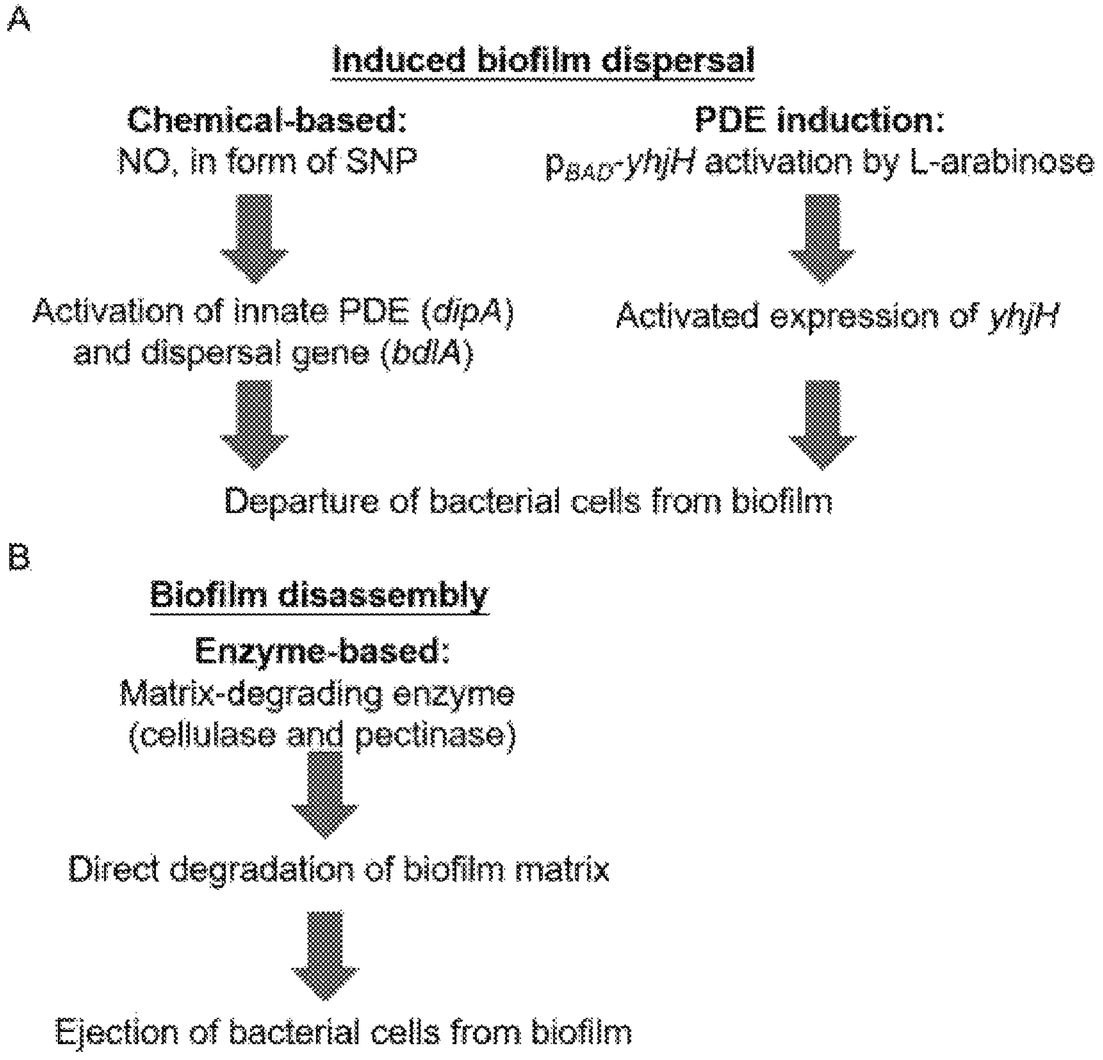
FIG. 6 schematically depicts two proposed mechanisms of how biological agent is released from biofilm: (A) chemical-based (NO) versus PDE-induced biofilm dispersal via YhjH expression; and (B) enzymatic disassembly (EDA) via matrix-degrading enzyme (cellulase and pectinase).

To evaluate strategies for inducing dispersal in biofilms, dispersed cells were generated from biofilms by reducing c-di-GMP based on chemical stimuli with nitric oxide (NO) in the form of sodium nitroprusside (SNP) or by inducing the expression of plasmid-encoded YhjH PDE to degrade c-di-GMP (FIG. 6A). This would eliminate the possibility of pleiotropic effects caused purely by SNP treatment or YhjH PDE expression.

Figure 7:
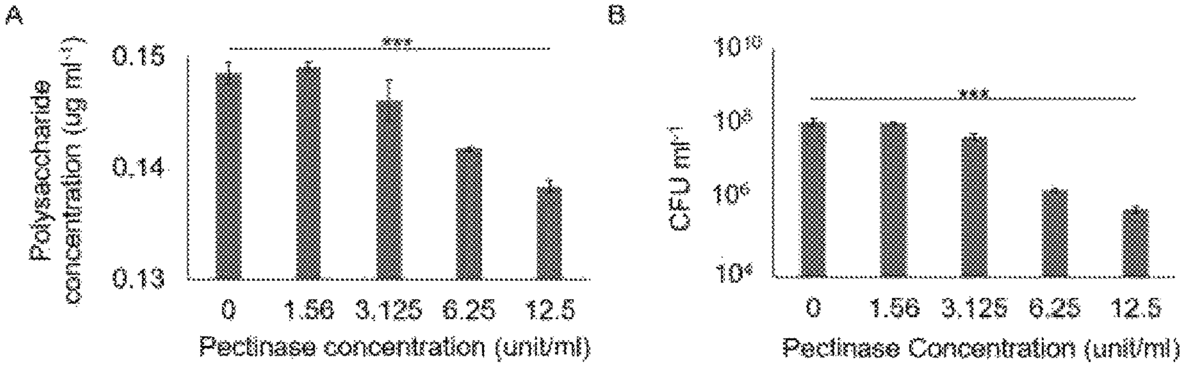
FIG. 7 shows that pectinase degrades one of the exopolysaccharides, Psl: (A) polysaccharide concentration after pectinase treatment. (B) CFU of biofilm treated with pectinase, where the means and s.d. from triplicate experiments were shown; ***P<0.001.
Figure 8:
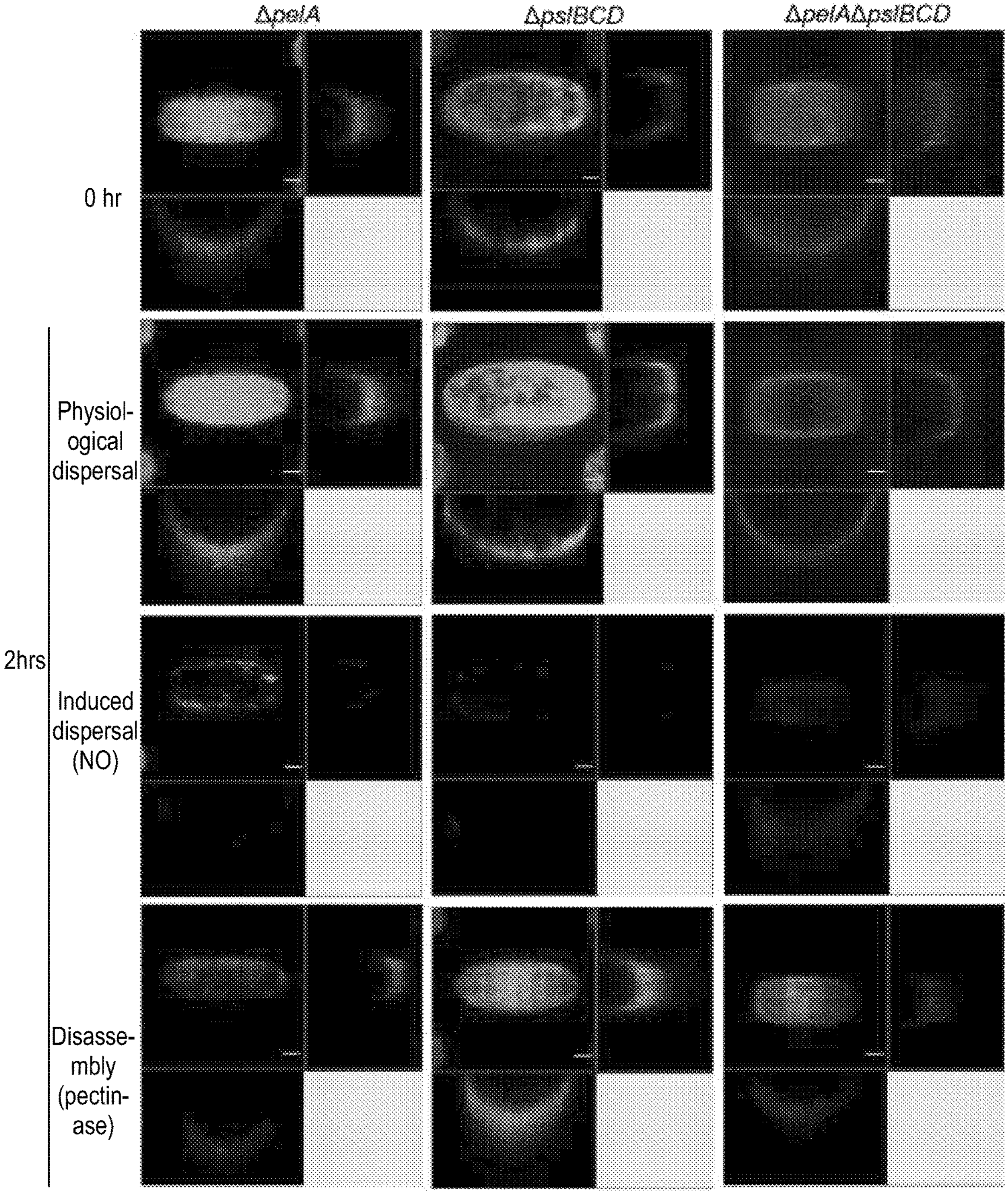
FIG. 8 shows fluorescence images of ΔpelA, ΔpslBCD, and ΔpelAΔpslBCD biofilms after 2 hrs of biofilm NO-based CID and pectinase-based EDA, where the scale bar is 50 μm.
Figure 9:
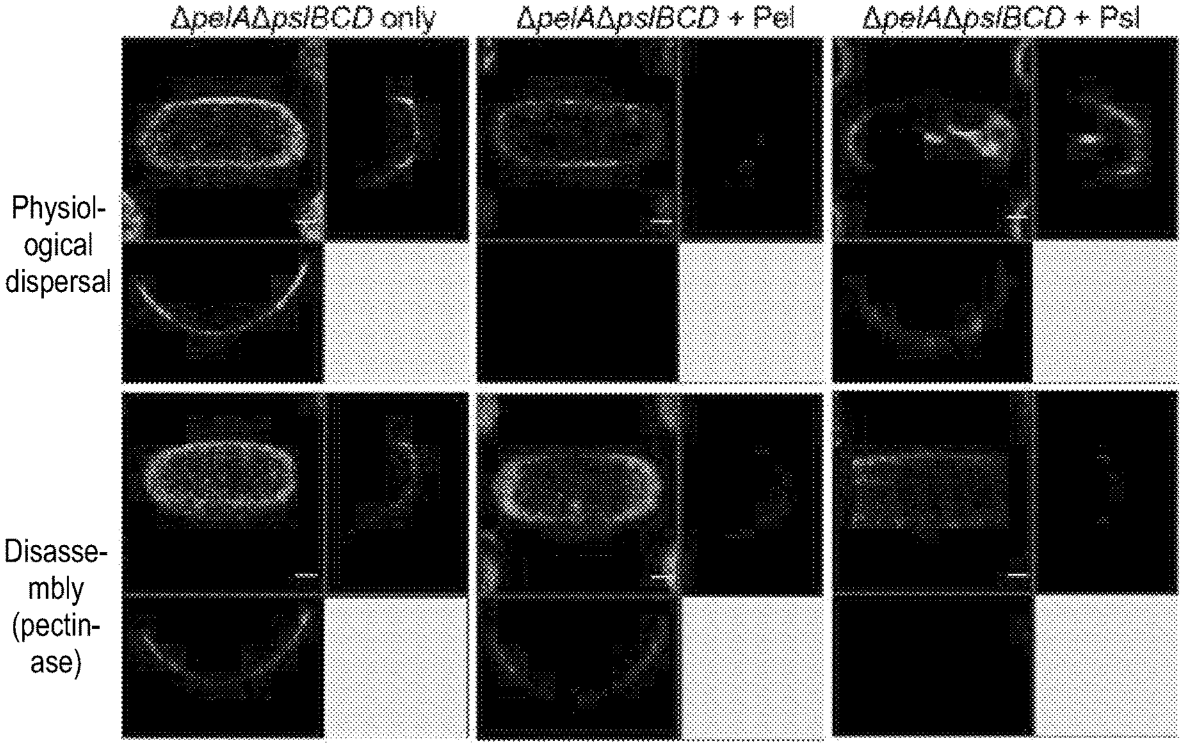
FIG. 9 shows fluorescence images of ΔpelAΔpslBCD biofilms with/without the exogenous coating of Pel (another exopolysaccharides) or Psl in microwells after 2 hrs of pectinase-based EDA, where the scale bar is 50 μm.

For biofilm disassembly, biofilm disassembled cells were generated by enzymatic treatment with two different enzymes, cellulase and pectinase (FIG. 6B). Pectinase could degrade Psl exopolysaccharide in *P. aeruginosa* biofilms (FIG. 7). The Psl-containing ΔpelA mutant biofilm would then be dispersed by pectinase, while Psl-deficient ΔpslBCD mutant biofilm remained intact after pectinase treatment (FIG. 8). Exogenous addition of Psl to ΔpelAΔpslBCD mutants, which were biofilm-deficient, enabled biofilm formation. Biofilm formation could then be abrogated by pectinase treatment (FIG. 9), indicating that biofilm disassembly required enzymes that specifically degrade biofilm matrix components.

Figure 10A:
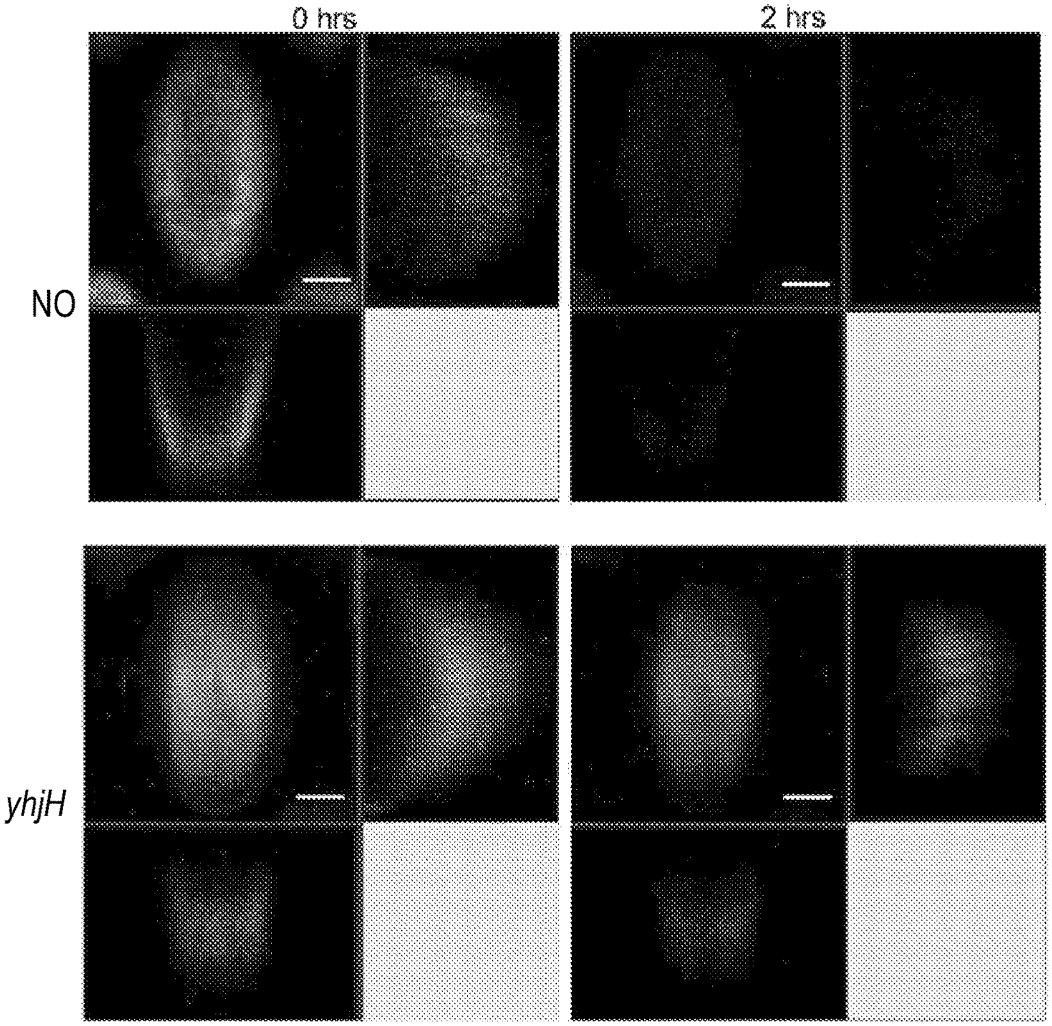
FIG. 10A shows fluorescence images of biofilms formed in the first chamber of the BDR microfluidic device exposed to a nitric oxide (NO) donor (sodium nitroprusside, or SNP) (upper row) and biofilms formed in the first chamber of the BDR microfluidic device by bacteria expressing plasmid-encoded YhjH PDE (lower row) over 2 hrs, where the scale bar is 50 μm.
Figure 10B:
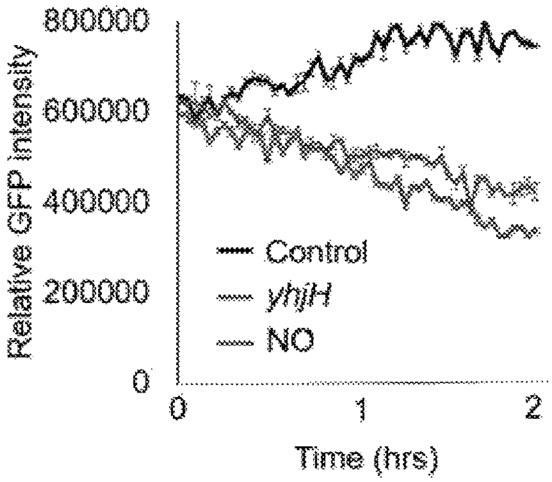
FIG. 10B shows the change of biofilm biomass (GFP intensity) over time as in the lower row of FIG. 10A compared with a control (ABTGC media only)
Figure 10C:
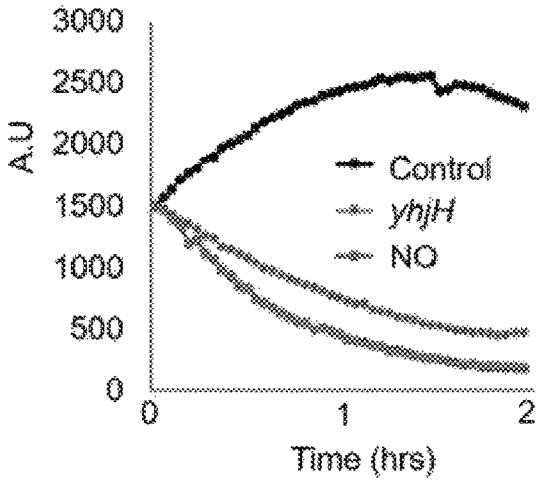
FIG. 10C shows a mathematical modelling of the biofilm dispersal according to the chemicals depicted in FIG. 10A.
Figure 10D:
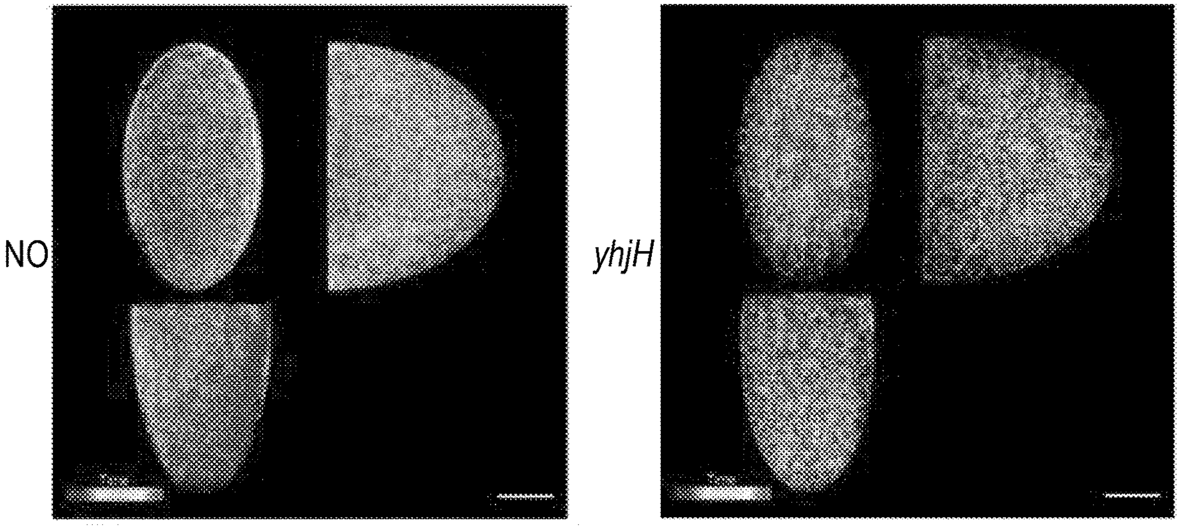
FIG. 10D shows the time-resolved cell trajectories of induced biofilm dispersal in the first chamber of the BDR microfluidic device by NO (left panel) and plasmid-encoded YhjH PDE (right panel) as in the upper and lower rows of FIG. 10A, respectively, where the color scheme from purple to red indicates chronological order from 0 hr to 2 hrs.
Figure 10E:
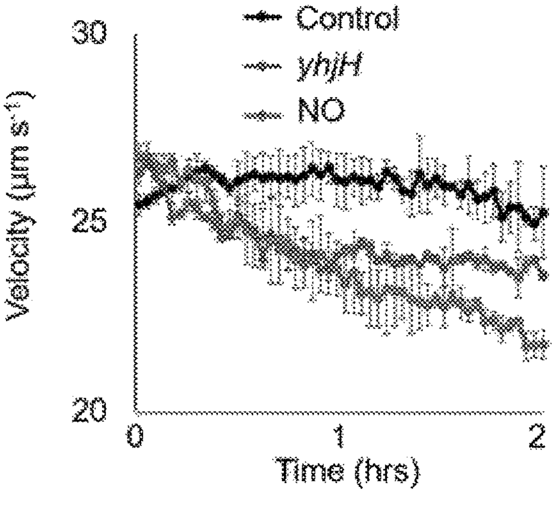
FIG. 10E shows the speed of biofilm dispersed cells over time as in the lower row of FIG. 10*a* compared with the control, where the means and s.d. from triplicate experiments were shown.

During the induced biofilm dispersal, bacterial cells left the biofilms within 2 hrs (FIGS. 10A and 10B). Mathematical models for inducing biofilm dispersal revealed an exponential decay in biofilm biomass, indicating that many bacteria dispersed in the initial stage and slowed down in the later stage (FIG. 10C). The majority of bacteria dispersed from the biofilm and entered the media space of the microwells within the 1$^{st}$ hour, but completely departed from the microwells within the 2$^{nd}$ hour (FIG. 10D). A similar trend of CID bacterial motility was observed compared to that of physiologically dispersed cells during the initial phase, but CID bacterial motility decreased significantly over time, which was attributed to the majority of bacteria leaving the microwells by the end of 2 hrs (FIG. 10E).

EDA Leads to the Explosive Release of Bacterial Aggregates

Figure 11A:
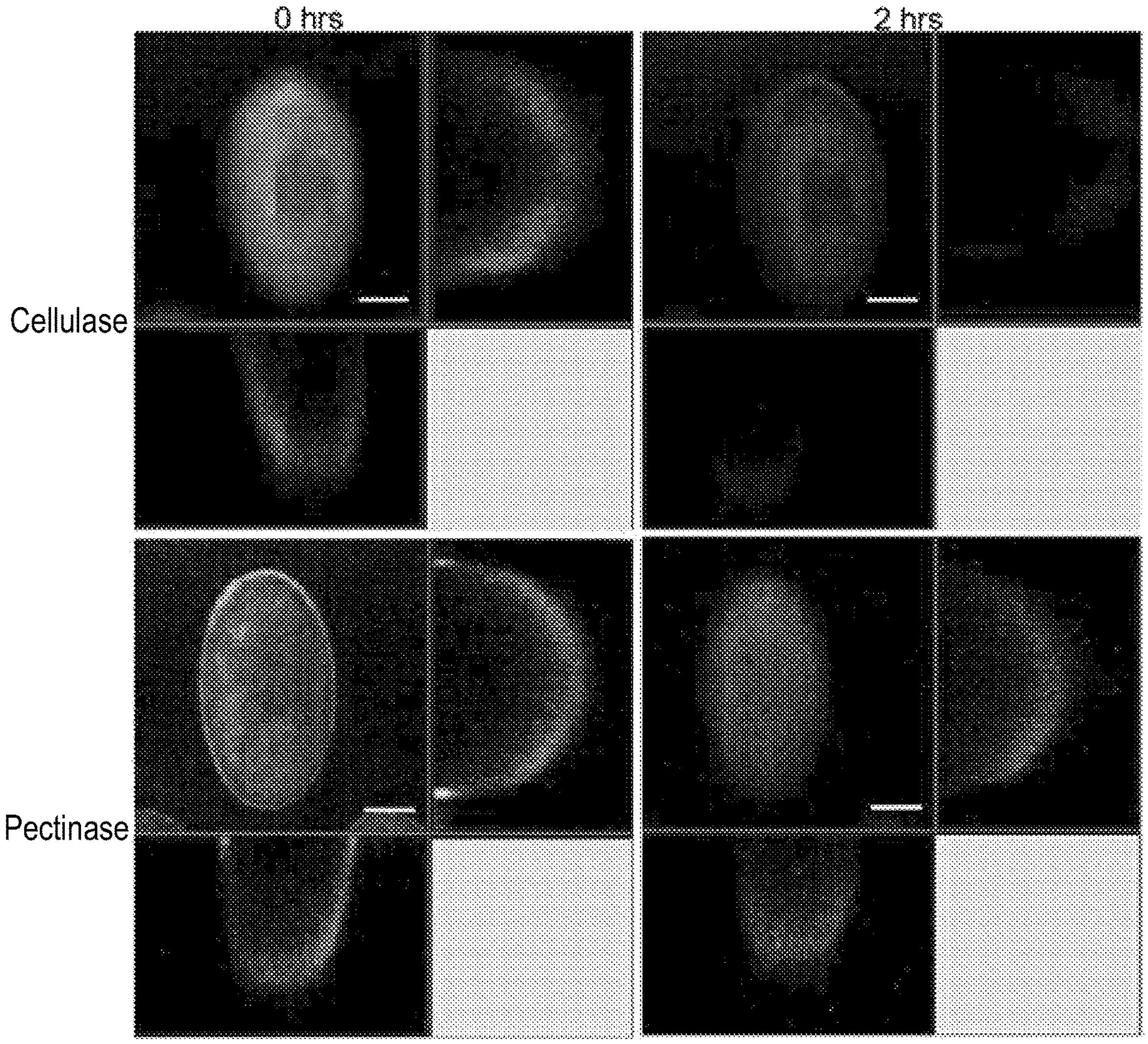
FIG. 11A shows fluorescence images of biofilms formed in the first chamber of the BDR microfluidic device exposed to cellulase (upper panel) and pectinase (lower panel) over 2 hrs, respectively.
Figure 11B:
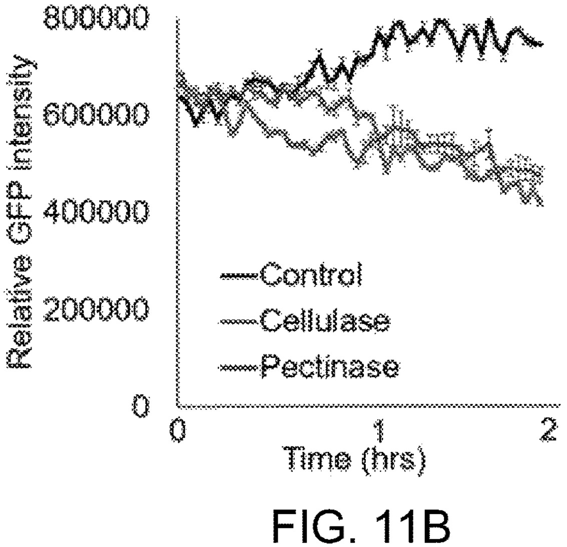
FIG. 11B shows the change of biofilm biomass (GFP intensity) over time as in FIG. 11A compared with a control (ABTGC media only)
Figure 11C:
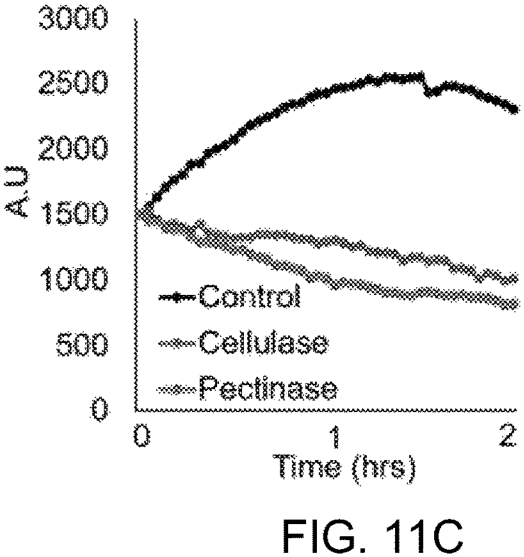
FIG. 11C shows a mathematical modelling of biofilm disassembly according to the enzymes depicted in FIG. 11A.
Figure 11D:
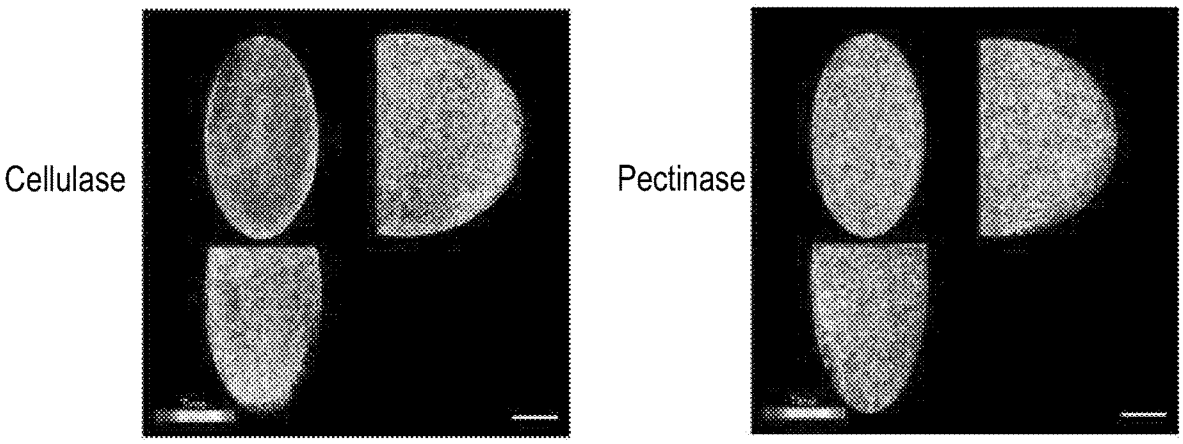
FIG. 11D shows a time-resolved cell trajectories of biofilm disassembly by cellulase (left panel) and pectinase (right panel), where the color scheme from purple to red indicated chronological order from 0 hr to 2 hrs.
Figure 11E:
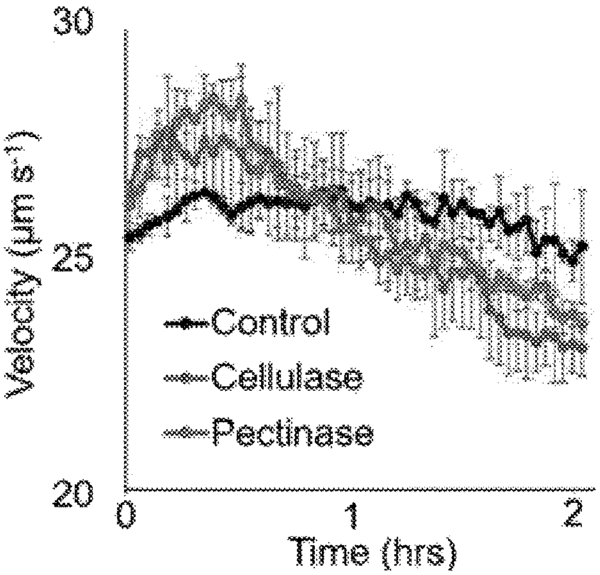
FIG. 11E shows the speed of biofilm disassembled cells over time as in FIG. 11A compared with the control, where the means and s.d. from triplicate experiments were shown.

It was found that EDA resulted in a continuous reduction of biofilm from top to bottom of the microwells (FIGS. 11A and 11B), indicating the action by enzymes (cellulase and pectinase) from the exterior to the interior of biofilms. Mathematical models for inducing biofilm disassembly revealed a polynomial decay in biofilm biomass, indicating that bacteria remained in the microwell longer and left the microwell slower than induced biofilm dispersal (FIG. 11C). Bacteria were retained in the microwells after biofilm EDA (FIG. 11D). The rate of biofilm disassembly accelerated, which was then followed by a rapid decrease in rate (FIG. 11E), resembling an initial explosive release of cells from the biofilms.

Bacteria Undergo Distinct Spatiotemporal Dynamics Between CID and EDA

Figure 12A:
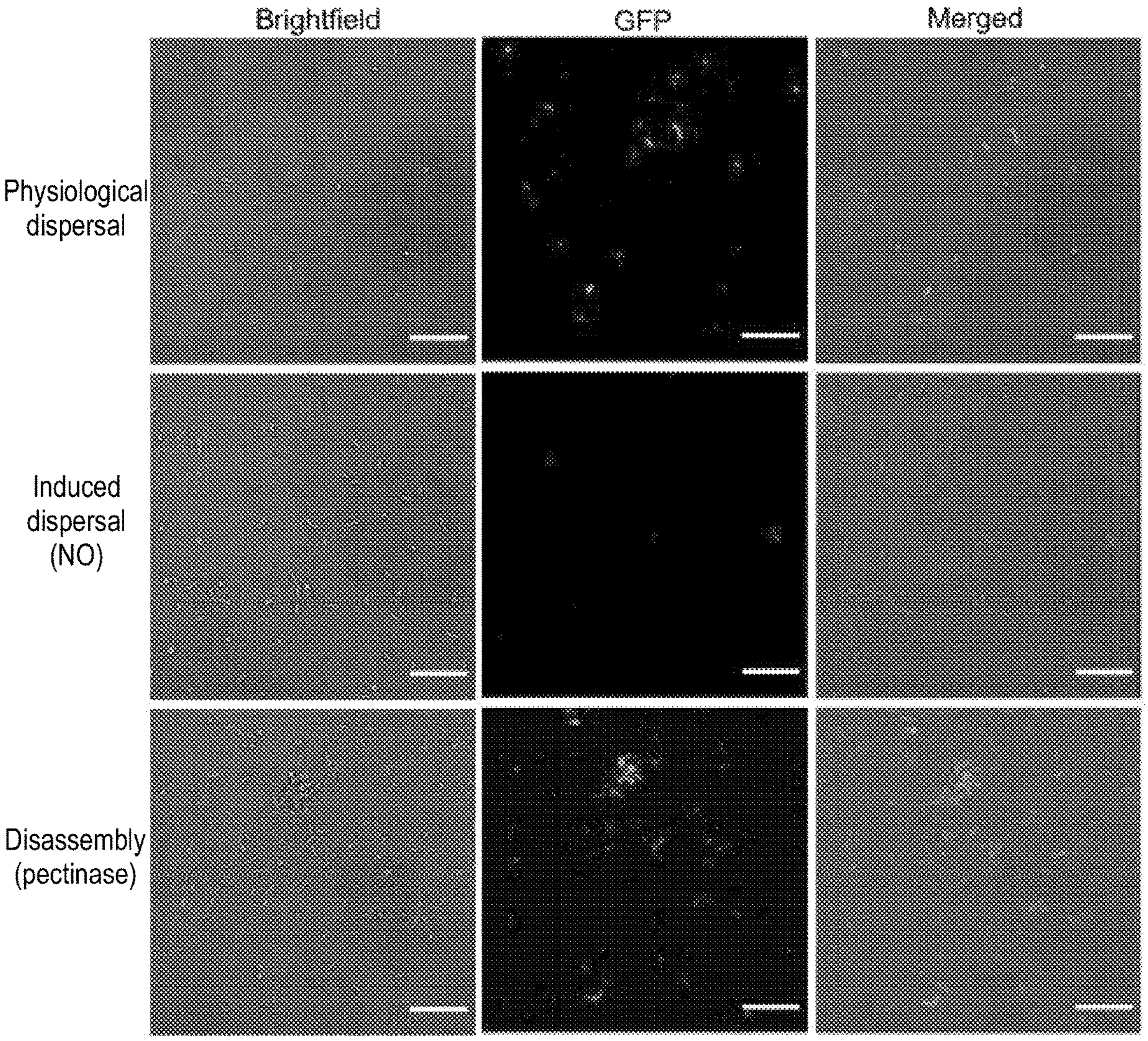
Figure 12B:
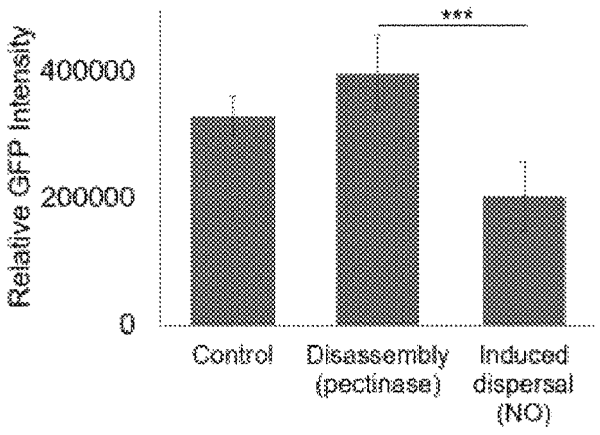
Figure 12C:
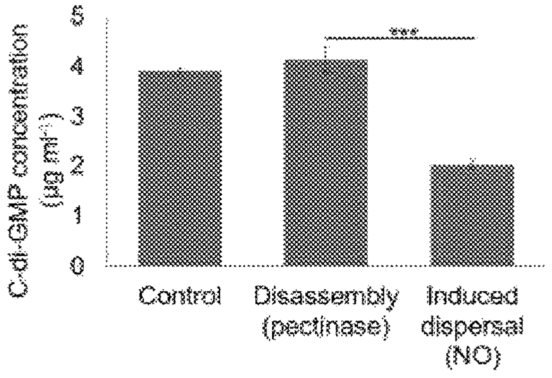

The next objective was to determine the mechanism underlying the difference between induced biofilm dispersal and biofilm disassembly, where CID appears to be actively undertaken by bacteria, whereas EDA may be a passive expulsion of bacteria from the matrix. There are several reasons to support the proposed underlying mechanism. It was observed that a decrease in intracellular c-di-GMP levels in bacteria occurred during the induction of biofilm dispersion, while biofilm-disassembled bacteria retained c-di-GMP levels similar to biofilm cells. This was supported by observing and measuring the GFP fluorescence intensity of the PAO1/$p_{cdrA}$-gfp biosensor (FIGS. 12A and 12B), and quantifying c-di-GMP levels with the ELISA assay (FIG. 12C).

Figure 12D:
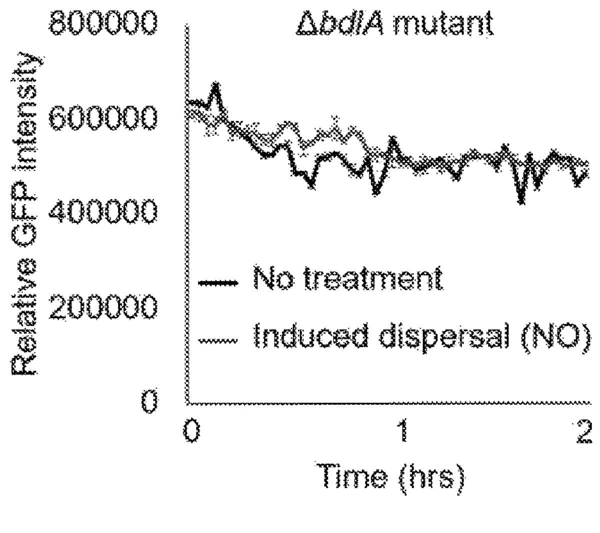
Figure 12E:
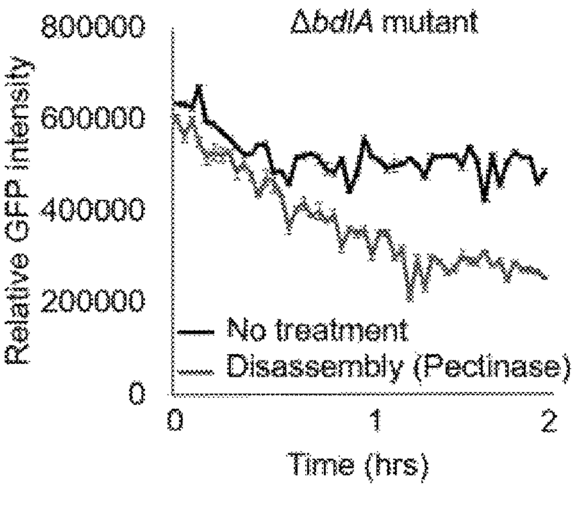
Figure 13:
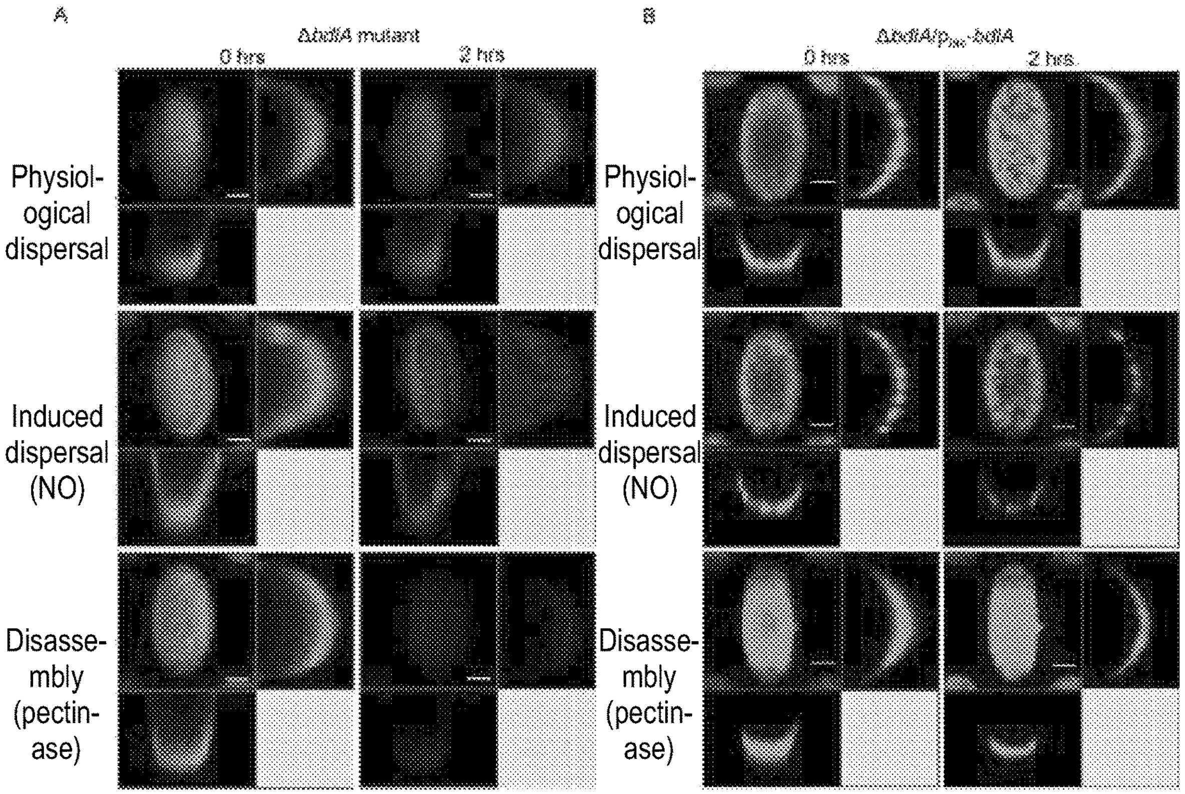
FIG. 13 shows fluorescence images of biofilms formed by (A) ΔbdlA mutant and (B) ΔbdlA/$p_{lac}$-bdlA complementation strain in the first chamber of the BDR microfluidic device, where each type of the biofilms was subject to physiological dispersal (upper row), chemical-induced dispersal by NO (middle row) and enzymatic disassembly by pectinase (lower row), where the scale bar is 50 μm.

This was also reflected in the role of the c-di-GMP signalling-controlled gene bdlA in biofilm dispersal. Therefore, it was found that the ΔbdlA mutant could not undergo induced biofilm dispersal but could still be released by pectinase during biofilm disassembly (FIG. 12D, 12E, 13A). On the other hand, it was observed that the restoration of biofilm dispersal phenotype in the ΔbdlA/$p_{lac}$-bdlA complementation strain, as it could undergo induced biofilm dispersal by SNP (FIG. 13B).

Figure 12F:
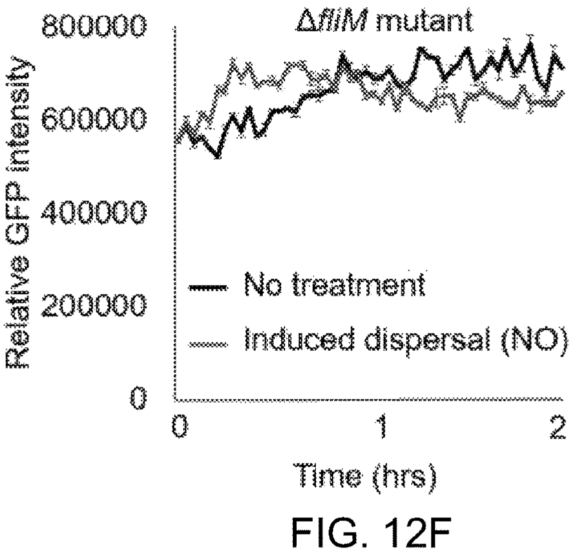
Figure 12G:
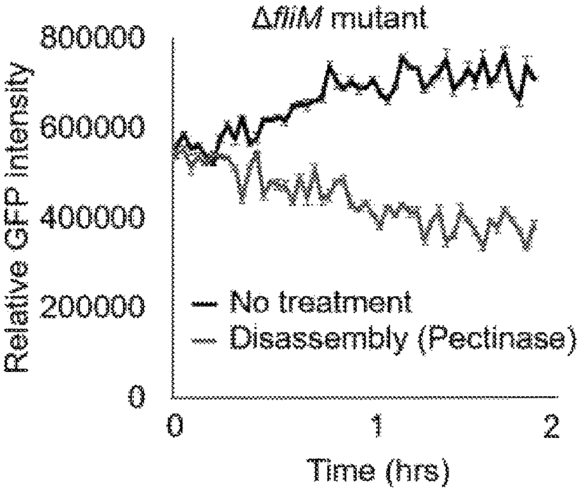
Figure 14:
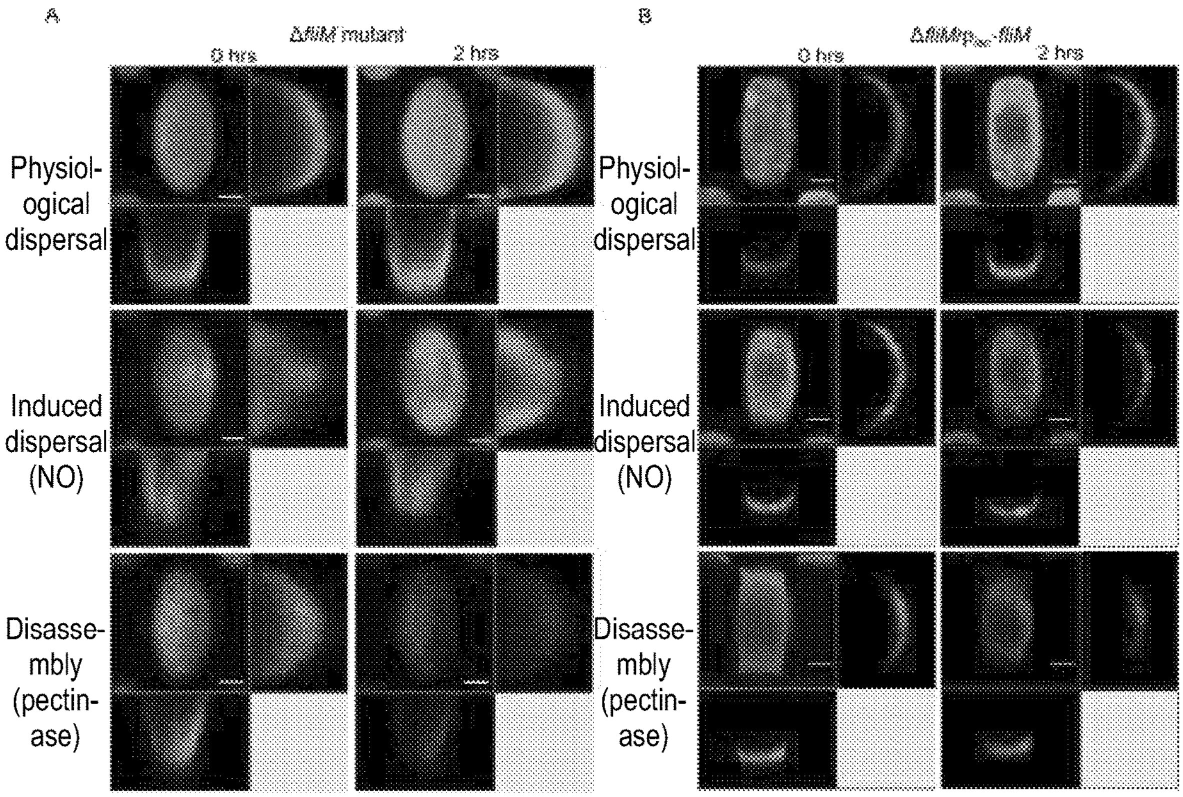
FIG. 14 shows fluorescence images of biofilms formed by (A) fliM mutant and (B) ΔfliM/$p_{lac}$-fliM complementation strain in the first chamber of the BDR microfluidic device, where each type of the biofilms was subject to physiological dispersal (upper row), chemical-induced dispersal by NO (middle row) and enzymatic disassembly by pectinase (lower row), where the scale bar is 50 μm.

Another difference related to flagellar motility, which was previously observed in biofilm-dispersed cells, is that they expressed flagella to actively depart from the biofilm. The flagella-deficient ΔfliM mutants lost the ability to leave the microwells during induced biofilm dispersal, but ΔfliM could still be released during biofilm disassembly (FIGS. 12F and 12G, FIG. 14A). The ΔfliM/$p_{lac}$-fliM complementation strain could undergo induced biofilm dispersal by SNP, indicating that flagella is important in active biofilm dispersal (FIG. 14B).

Figure 12H:
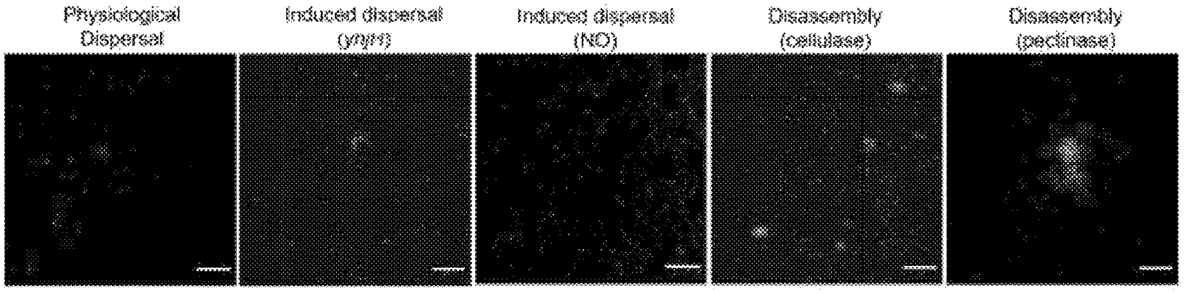

Furthermore, it was observed that biofilm-disassembled bacteria presented as small aggregates, instead of biofilm-dispersed bacteria which were predominantly single cells (FIG. 12H). This observation further suggested that bacteria released biofilm disintegration retains some aspects of their previous life as a biofilm.

Bacteria Generated from CID Cannot Recolonize Fresh Surfaces

Figure 15:
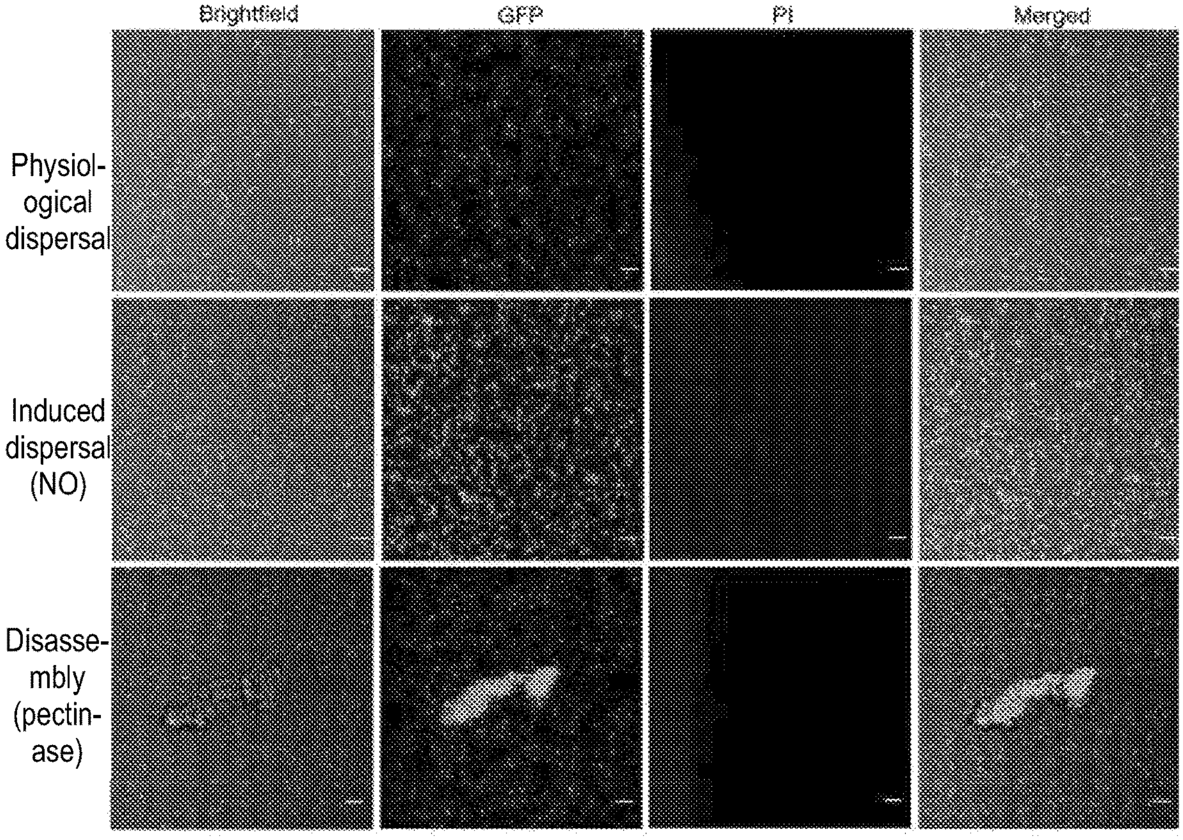
FIG. 15 shows images of the bacterial cells released from physiological dispersal, CID (NO-induced dispersal) or EDA (pectinase-induced disassembly) from brightfield (first left column), green fluorescence for GFP signals (second left column), red fluorescence for PI stain (second right column), and merged view (first right column), where the scale bar is 20 μm.
Figure 16A:
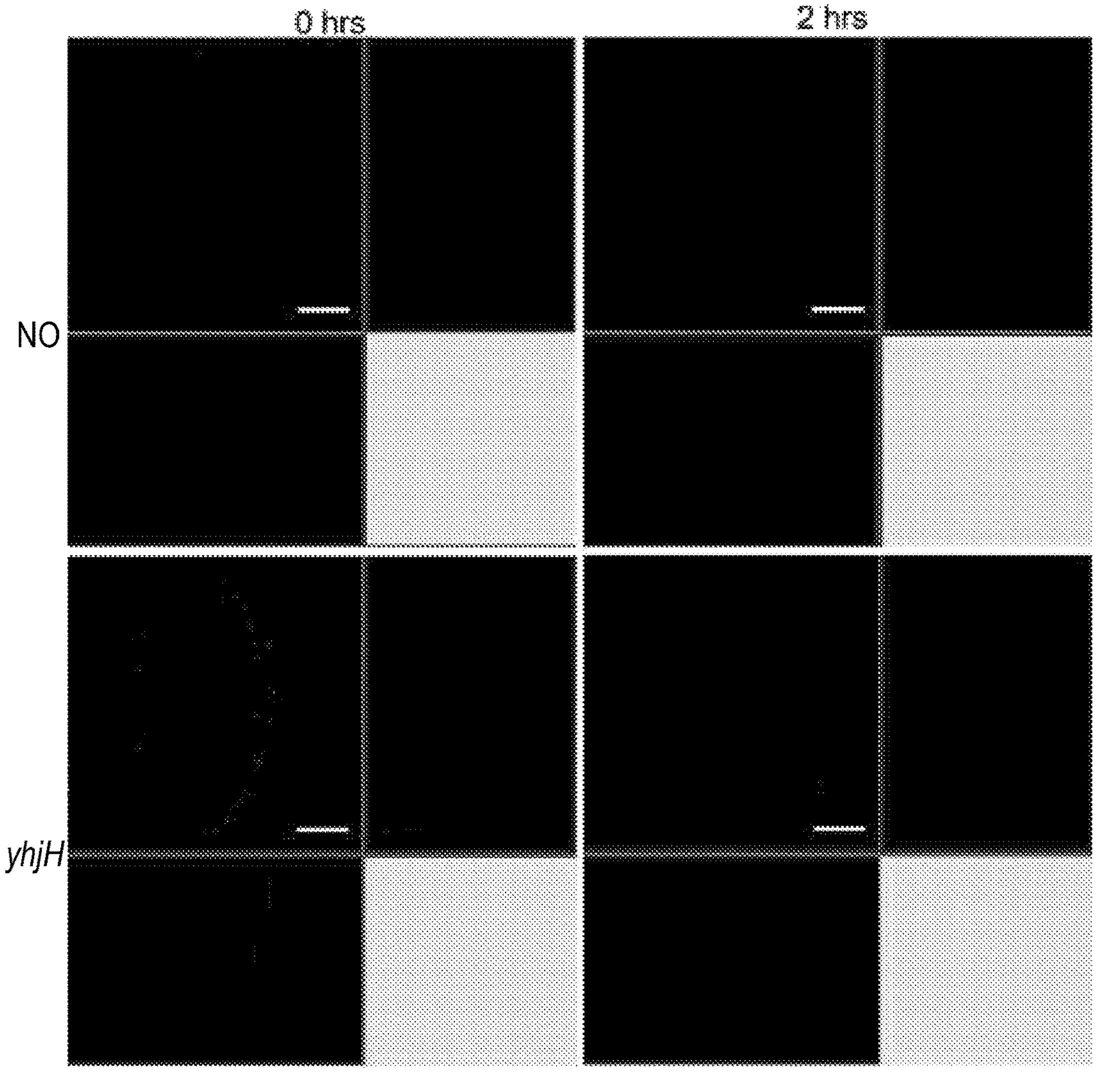
FIG. 16A shows fluorescence images of recolonized CID-released cells in the second chamber of the BDR microfluidic device from biofilms exposed to NO or plasmid-encoded YhjH PDE over 2 hrs, where the scale bar is 50 μm.
Figure 16B:
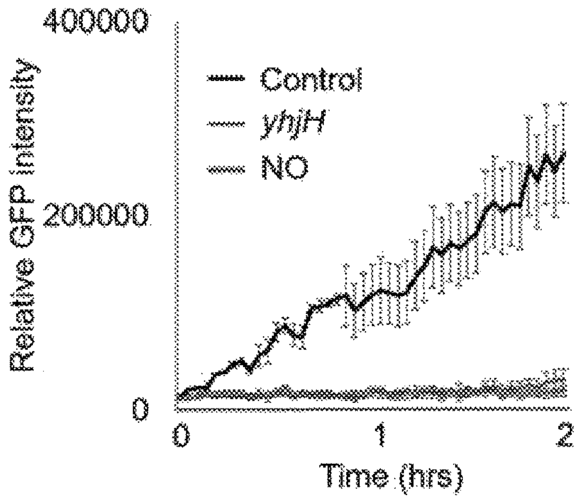
FIG. 16B shows the change in GFP intensity of biofilm biomass of the CID-released cells exposed to NO and the plasmid-encoded YhjH PDE, respectively, as in FIG. 16A over time compared with a control (ABTGC media only)
Figure 16C:
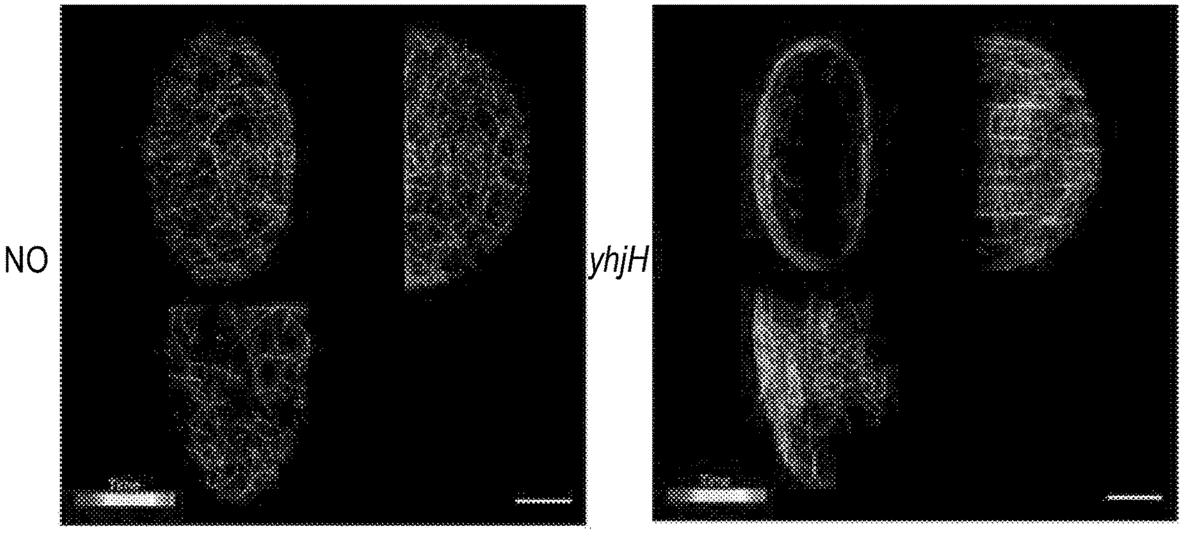
FIG. 16C shows time-resolved cell trajectories of recolonization by induced biofilm dispersed cells exposed to NO (left panel) and the plasmid-encoded YhjH PDE (right panel), respectively, where color scheme from purple to red indicated chronological order from 0 hr to 2 hrs.
Figure 16D:
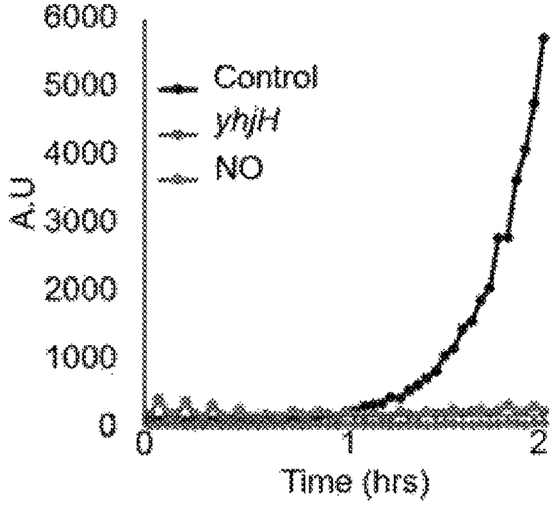
FIG. 16D shows that the mathematical modelling revealed biofilm dispersed cells recolonization follows no pattern.
Figure 16E:
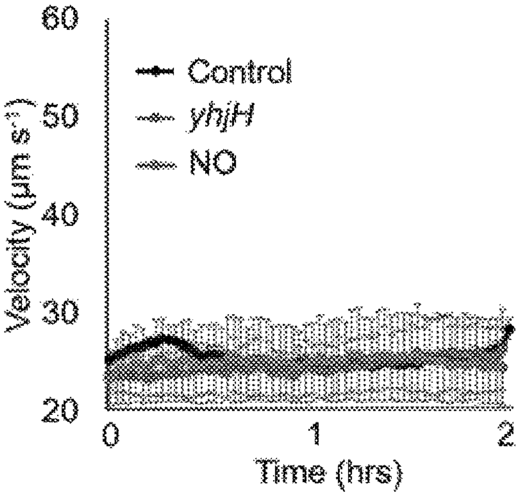
FIG. 16E shows the change of velocities of CID-released cells exposed to NO and the plasmid-encoded YhjH PDE, respectively, as in FIG. 16A over time compared with the control, where the means and s.d. from triplicate experiments were shown.

The biofilm life cycle usually involves bacterial recolonization of new areas. Since biofilm dispersal differs from biofilm disassembly, the next objective was to investigate whether bacterial cells generated from both approaches would have differing recolonization dynamics. It is important to note that bacteria released from biofilm dispersal and disassembly remained viable, where PI dead stain did not label the bacterial cells (FIG. 15), indicating that their recolonization was not affected by cell death. While bacteria derived from physiological biofilm dispersal could rapidly colonize in the secondary chambers, bacteria released due to c-di-GMP-reduced CID could not colonize on the interior surface of the microwells of the secondary chambers (FIG. 16A-16D), despite the ability of biofilm dispersed bacteria to maintain consistent speeds in general (FIG. 16E). This could be attributed to the fact that induced biofilm dispersed cells maintained their physiology for at least 6 hrs, so they could not recolonize in the microwells.

Bacterial Aggregates from Biofilm Disassembly Slowly Recolonized New Areas

Figure 17A:
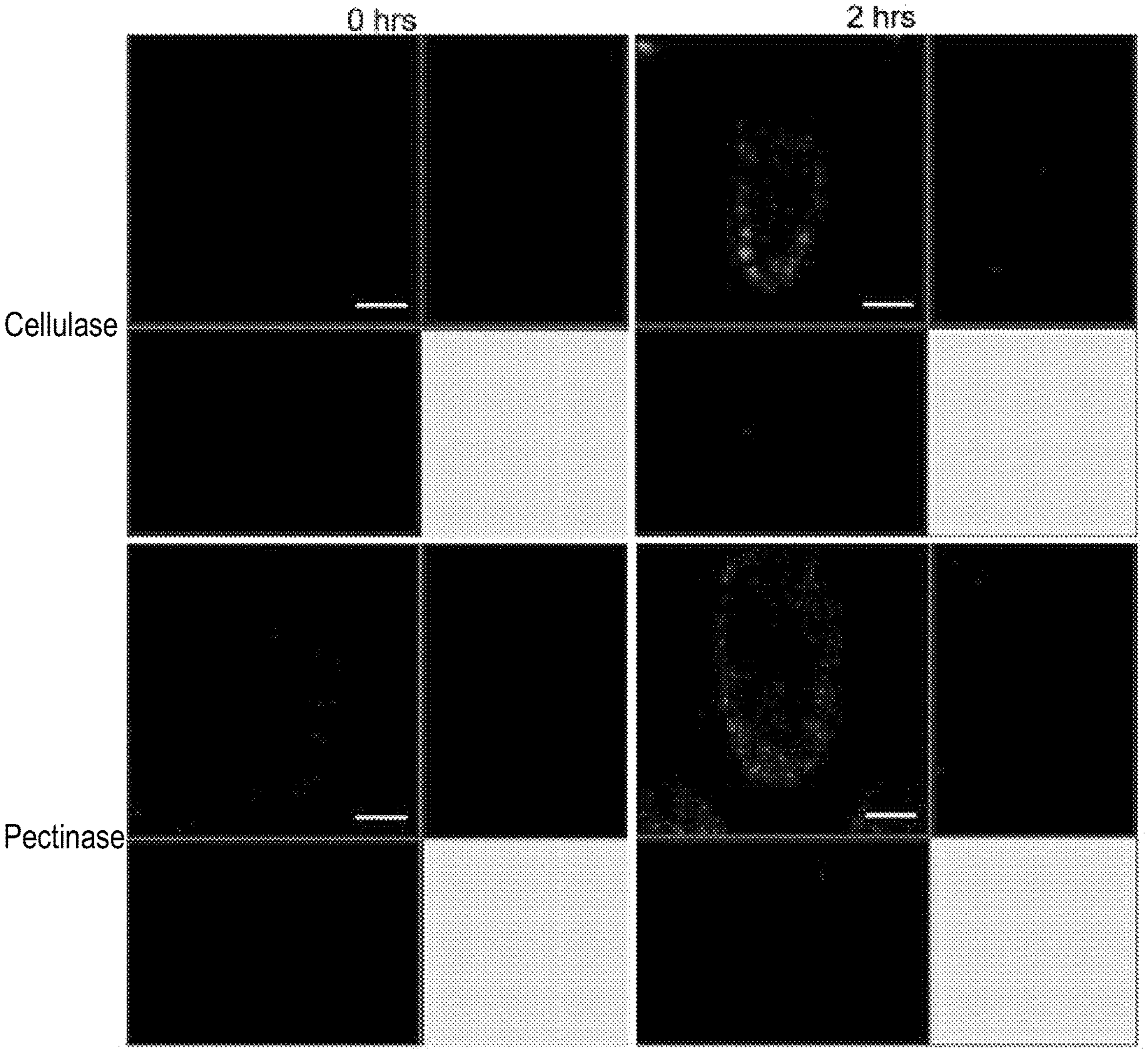
FIG. 17A shows fluorescence images of recolonized EDA-released cells in the second chamber of the BDR microfluidic device from biofilms exposed to cellulase (upper row) and pectinase (lower row), respectively, over 2 hrs, where the scale bar is 50 μm.
Figure 17B:
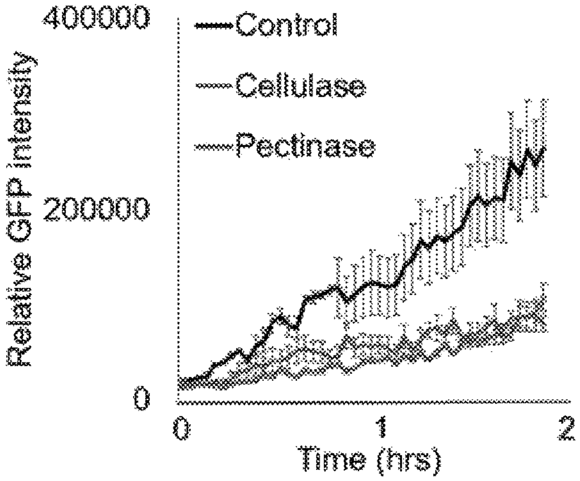
FIG. 17B shows the change in GFP intensity of biofilm biomass of the EDA-released cells exposed to cellulase and pectinase, respectively, as in FIG. 17A over time compared with a control (ABTGC media only)
Figure 17C:
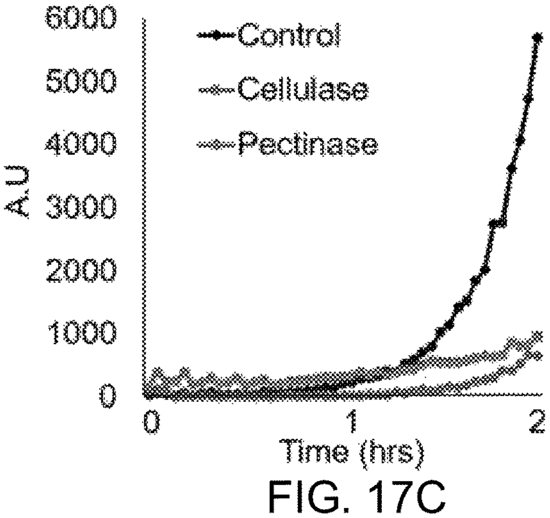
FIG. 17C shows that the mathematical modelling revealed biofilm disassembled cell recolonization follows an exponential pattern.
Figure 17D:
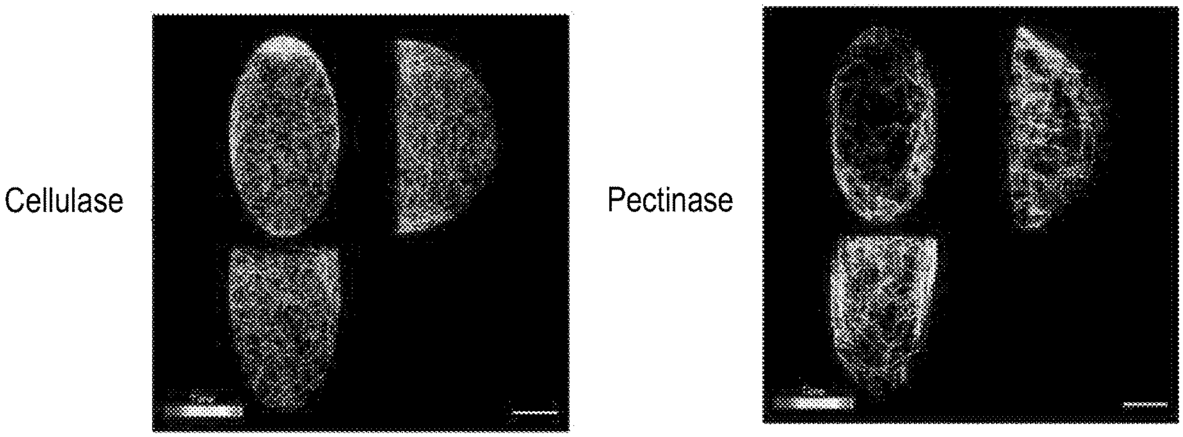
FIG. 17D shows time-resolved cell trajectories of recolonization by biofilm-disassembled cells exposed to cellulase (left panel) and pectinase (right panel), respectively, where color scheme from purple to red indicated chronological order from 0 hr to 2 hrs.
Figure 17E:
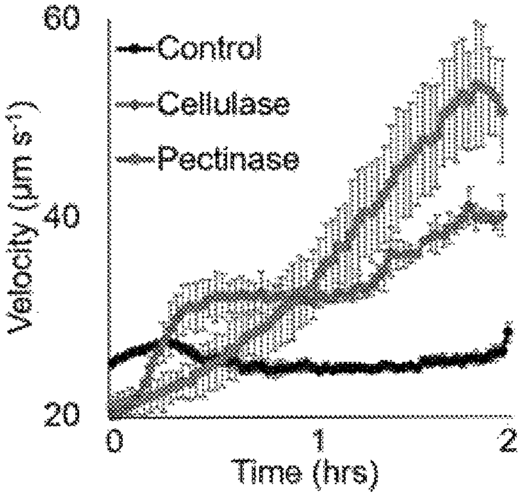
FIG. 17E shows the change of velocities of EDA-released cells exposed to cellulase and pectinase, respectively, as in FIG. 6*a* over time compared with the control, where the means and s.d. from triplicate experiments were shown.

Compared to CID-released bacteria, EDA-released bacteria could colonize in the secondary chamber, albeit at a lower magnitude than physiological dispersal over time (FIGS. 17A and 17B). The proposed mathematical model showed an exponential recolonization of biofilm disassembled bacteria, but still at a lower magnitude than physiological dispersal (FIG. 17C). Recolonization of these EDA-released bacteria occurred mainly in the $2^{nd}$ hour (FIG. 17D), as they required some time to migrate from the primary chamber to the secondary chamber. This corresponded to faster recolonization of bacteria expelled from the biofilm (FIG. 17E), when they were initially released from the biofilm at high speeds.

In summary, the present disclosure unveils the new mechanisms underlying biofilm CID and EDA by employing spatiotemporal imaging, mutagenesis, biosensor quantification and mathematical modelling. Bacteria resulting from CID are usually single-celled, where they require bdlA gene for dispersal and employ flagella to leave biofilms. They cannot immediately recolonize on fresh surfaces, which corroborated the present inventors' previous study that the dispersed cells maintained their physiology for 6 hrs (Chua et al., 2014). However, EDA of biofilm releases "biofilm-like" bacteria aggregates, bypassing the need for activating biofilm dispersal genes and motility apparatus. They can recolonize fresh surfaces, albeit at lower efficiencies than physiological biofilm dispersal, possibly due to the low metabolism of biofilm cells Table 1 below summarizes the major differences between induced biofilm dispersal and biofilm disassembly.

TABLE 1

| | Induced biofilm dispersal | Biofilm disassembly |
|---|---|---|
| | Biofilm dispersal | |
| Biofilm biomass | Exponential decay over time | Consistent reduction over time |
| Mechanism | Biofilm dispersal genes are required | Degradation of biofilm matrix |
| Bacterial velocity | Consistent as motile cells, followed by gradual reduction in speed | Higher initial speed than motile cells, followed by reduction in speed |
| Flagella required | Yes | No |
| Single cell or aggregate | Mostly single cells | Mostly small aggregates |
| | Recolonization | |
| Recolonization | Minimal | Low but detectable levels |
| Bacterial velocity | Consistent as motile cells | Higher speeds than motile cells |

Figure 18A:
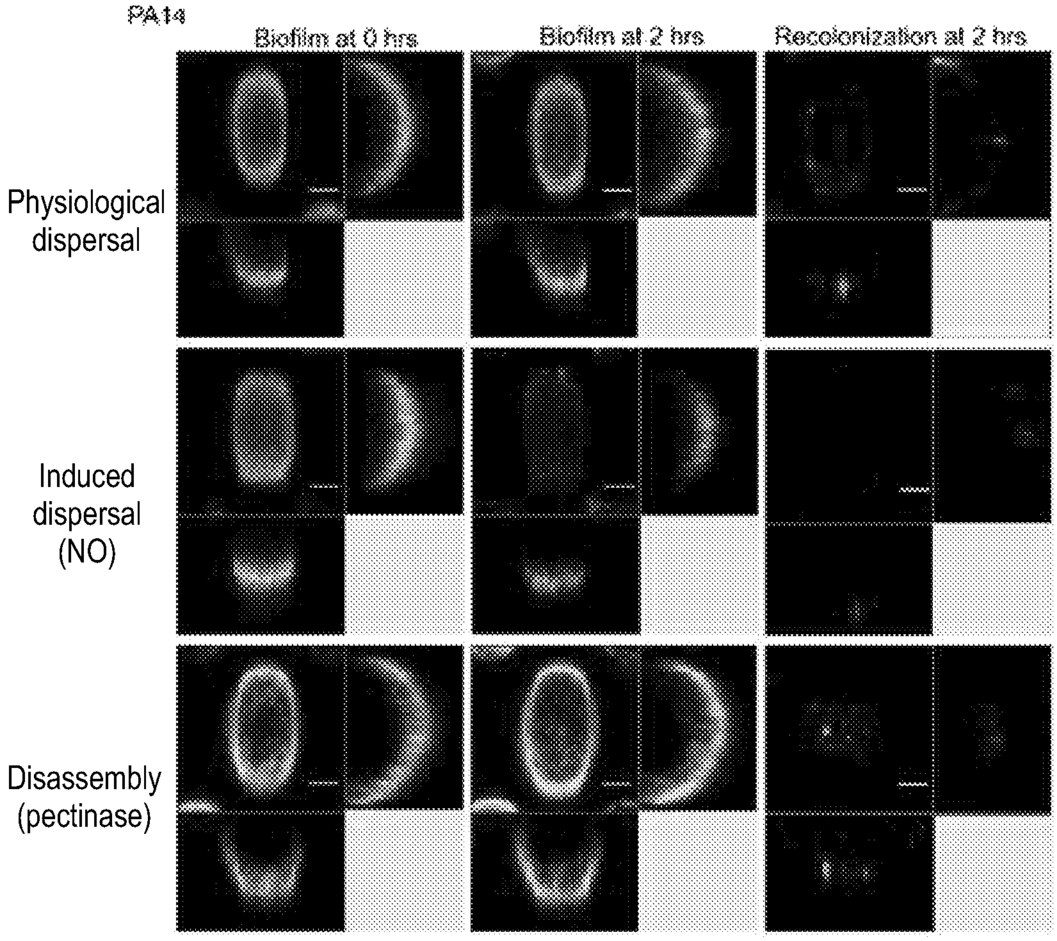
FIGS. 18A-18C shows fluorescence images of biofilm formed by different *P. aeruginosa* strains including PA14
Figure 18B:
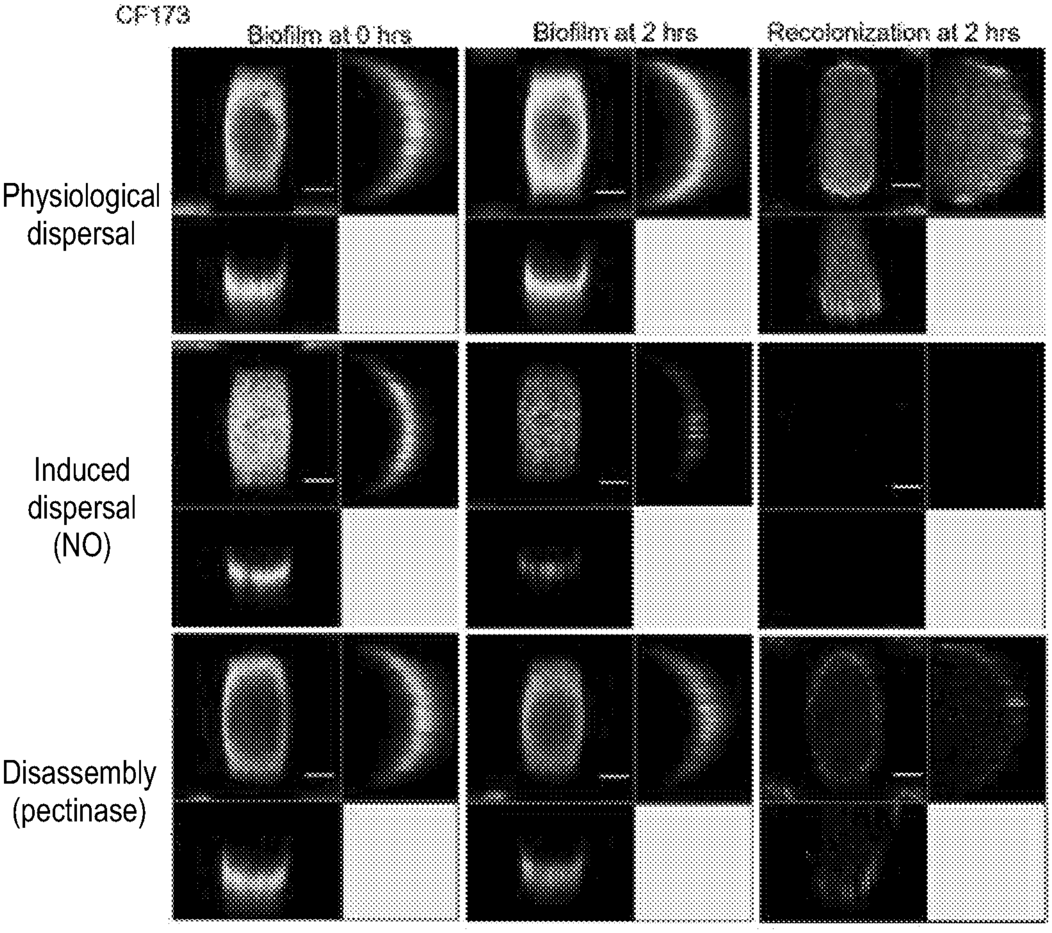
Figure 18C:
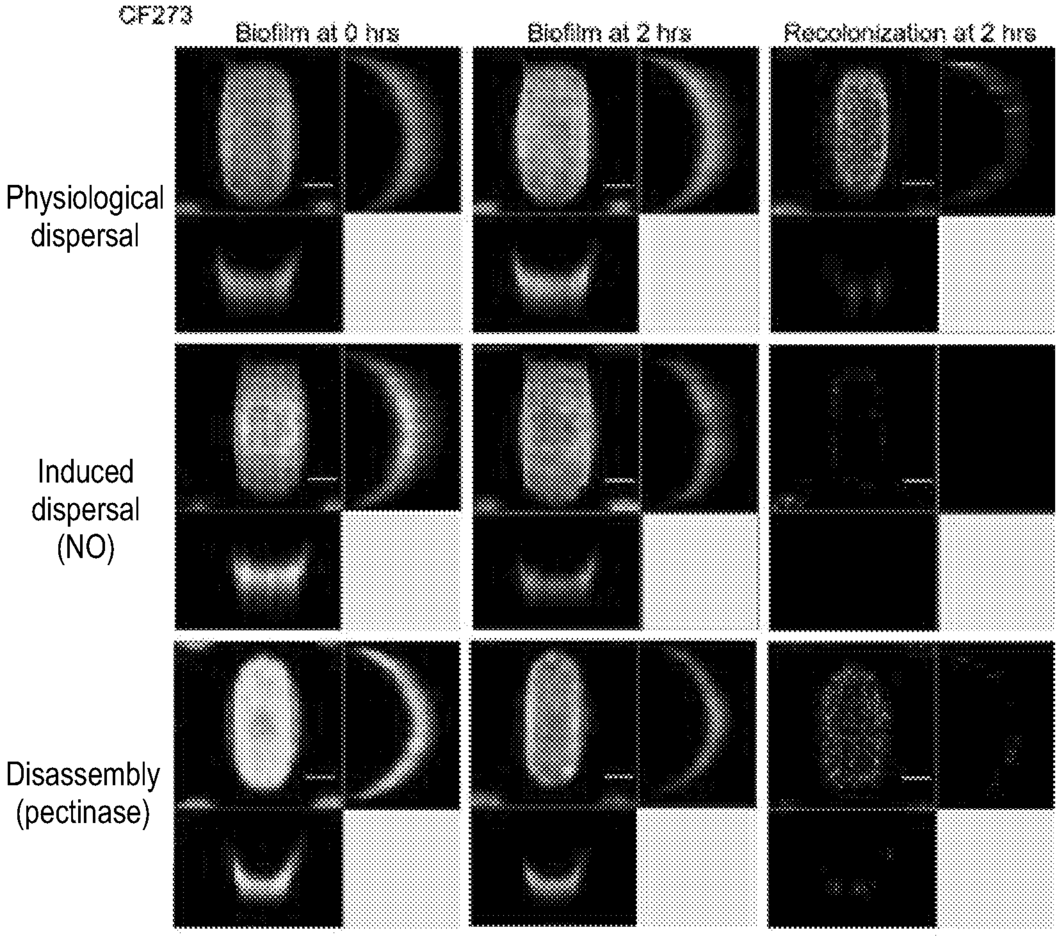

Similar Dispersal and Recolonization Behavior Adopted by *P. aeruginosa* Clinical Isolates To evaluate if the findings in PAO1 could be applicable to other *P. aeruginosa* strains, the effects of biofilm CID and EDA on PA14 (Table 4) and 2 other clinical isolates (CF173 and CF273) (Chua et al., 2016) were evaluated. For PA14, CID could induce biofilm dispersal, with minimum recolonization of dispersed bacteria. However, as PA14 possessed the ability to produce Pel but not Psl, pectinase-mediated EDA was not very effective in breaking down the biofilm matrix, resulting in minimal bacterial aggregates which recolonized the surface of secondary chamber (FIG. 18A). Till date, no Pel-degrading enzymes was commercially available for testing. As for CF173 and CF273, they were pro-biofilm-forming clinical isolates collected from cystic fibrosis patients, so higher concentrations of antibiofilm agents were employed to elicit CID and EDA. Nonetheless, similar trends were observed between both clinical isolates and PAO1, where CID-generated bacteria could not recolonize in fresh areas and EDA-generated bacterial aggregates could recolonize in the secondary chamber (FIGS. 18B and 18C). This indicated that our findings are common across different *P. aeruginosa* strains, albeit different concentrations of antibiofilm agents may be required.

Unique Characteristics of Biofilm-Released Bacteria Determine the Fate of Disease Dissemination Since CID and EDA could lead to different fates in bacterial migration and subsequent recolonization of fresh surfaces, the next objective was to evaluate whether disseminated bacteria could cause infections in both in vitro human lung 3D-spheroids and in vivo *C. elegans* models. The lung spheroid culture model is a clinically relevant model for personalized medicine and it can recapitulate similar findings in animals and humans. *C. elegans* is a common animal model used to study *P. aeruginosa* pathogenesis, and its small size and transparency are advantageous in establishing animal models in microfluidics models.

Figure 19A:
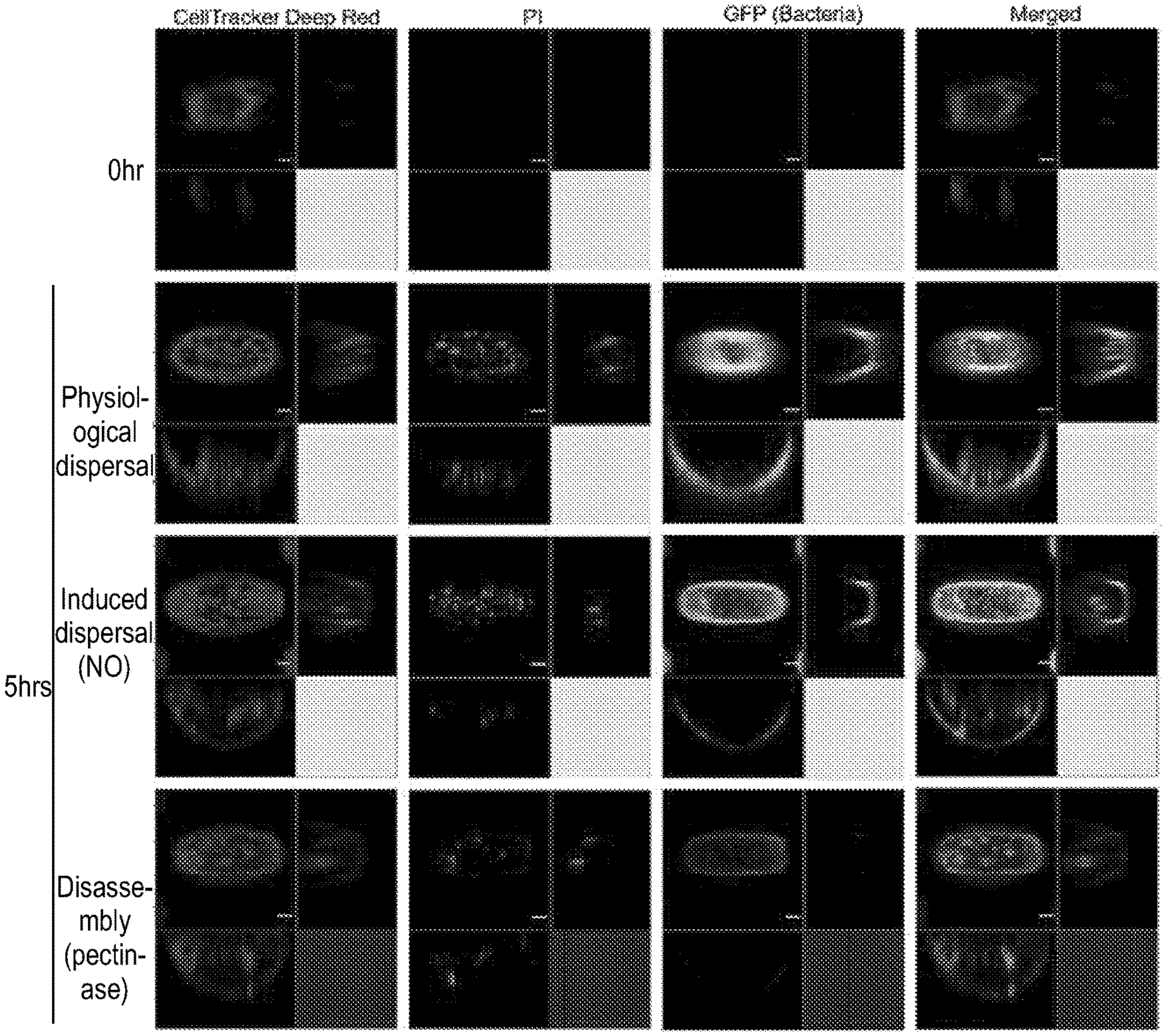
FIG. 19A shows fluorescence images of human lung spheroids exposed to bacteria released from biofilms through CID (NO) or EDA (pectinase) for 5 hrs compared with those exposed to a positive control (bacteria released from physiological dispersal), where the scale bar is 50 μm.
Figure 19B:
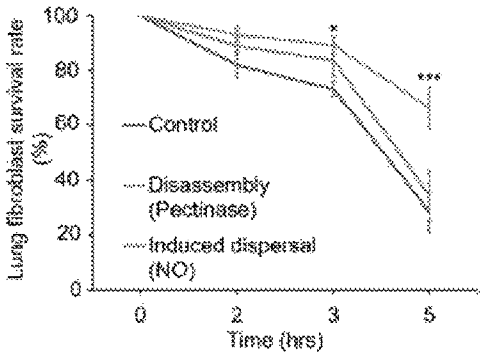
FIG. 19B shows survival rate of the human lung spheroids after exposure to different groups of bacteria released through CID or EDA according to FIG. 19A compared with a positive control, where the means and s.d. from triplicate experiments were shown; ***$p<0.001$; *$p<0.05$.
Figure 19C:
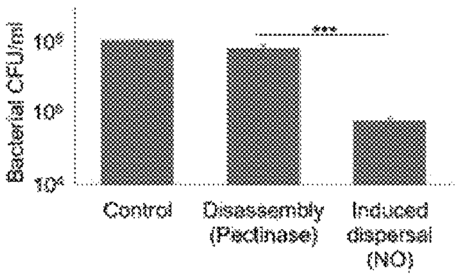
FIG. 19C shows bacterial numbers (CFU/ml) on the human lung spheroids exposed to different groups of bacteria released through CID or EDA according to FIG. 19A compared with a positive control, where the means and s.d. from triplicate experiments were shown; ***$p<0.001$.
Figure 19D:
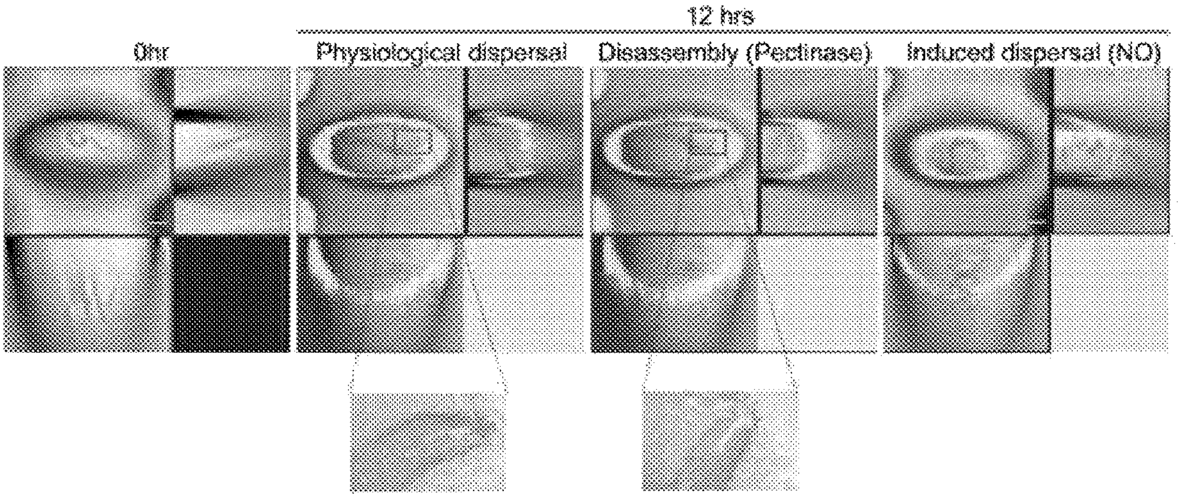
FIG. 19D shows merged phase-contrast and fluorescence images of *C. elegans* in association with bacteria released from biofilm dispersal (NO) or disassembly (pectinase) for 12 hrs compared with those exposed to a positive control (by physiological dispersal), where the scale bar is 50 μm, and two inset images show the localization of gfp-tagged bacteria in the *C. elegans* intestines exposed to the positive control (left inset image) and NO-induced dispersal (CID) bacteria (right inset image)
Figure 19E:
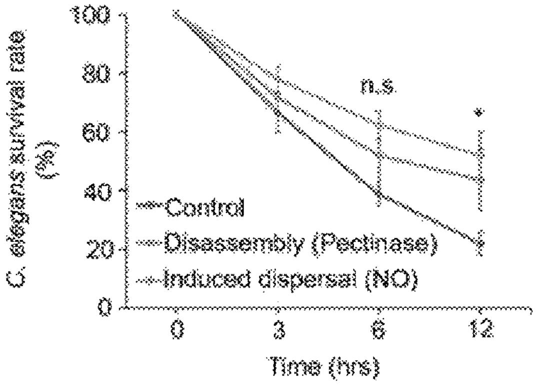
FIG. 19E shows survival rate of *C. elegans* after exposure to bacteria released from biofilm dispersal or disassembly as in FIG. 19A, where the means and s.d. from triplicate experiments were shown; *$p<0.05$; n.s: not significant.
Figure 19F:
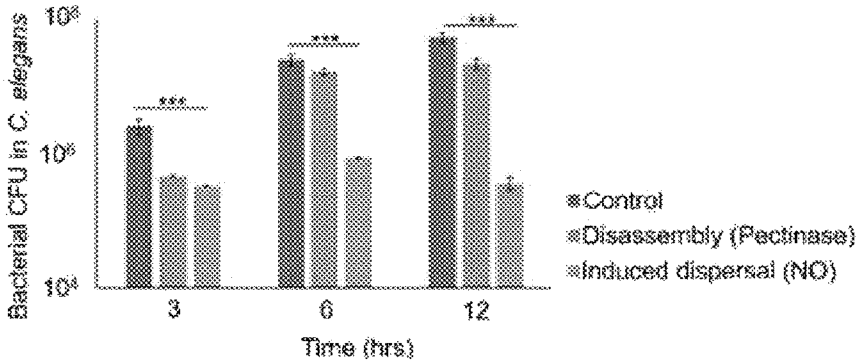
FIG. 19F shows bacterial numbers in the *C. elegans* intestines exposed to different groups of bacteria release through biofilm dispersal or disassembly according to FIG. 19A over time, where the means and s.d. from triplicate experiments were shown; ***$p<0.001$.

Under normal conditions, *P. aeruginosa* bacteria freshly released from biofilms could colonize on the lung spheroid cells (FIG. 19A-19C). The EDA cells could colonize on the lung spheroids at higher numbers and cause infections similarly to control cells (FIG. 19A-19C). However, CID cells could not colonize on the eukaryotic models at lower numbers, thereby causing minimal infections and killing cells (FIG. 19A-19C). These in vitro data were similar to those from the *C. elegans* infection model, where a lesser killing effect of CID cells on *C. elegans* than control was observed (FIG. 19D). This was attributed to minimal colonization of bacteria within the *C. elegans* intestine (FIG. 19E-19F). Hence, this provides insights into both antibiofilm strategies, which could be adopted in clinical settings.

The present disclosure supports some previous studies that the animals were found to tolerate CID in mouse models of biofilm infection (Christensen et al., 2013), whereas lethal septicaemia could occur in the animals infected with cells from biofilm EDA (Fleming et al., 2018). The present disclosure indicates that biofilm dispersal might be a better antibiofilm strategy than biofilm disassembly, where there was lower disease dissemination and damage to other organs by biofilm-dispersed cells than biofilm-disassembled cells.

Figure 21A:
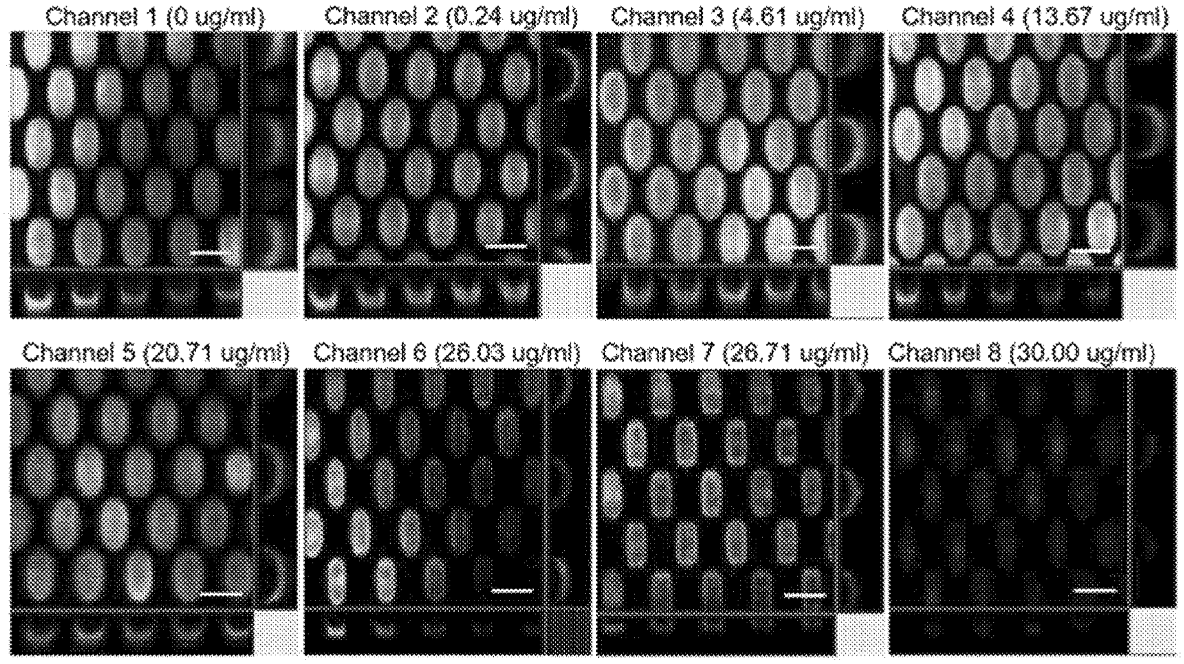
FIG. 21A shows fluorescence images of different biofilms treated with different concentrations of antibiotics from eight outlets of the concentration gradient generator of the BDR device.
Figure 21B:
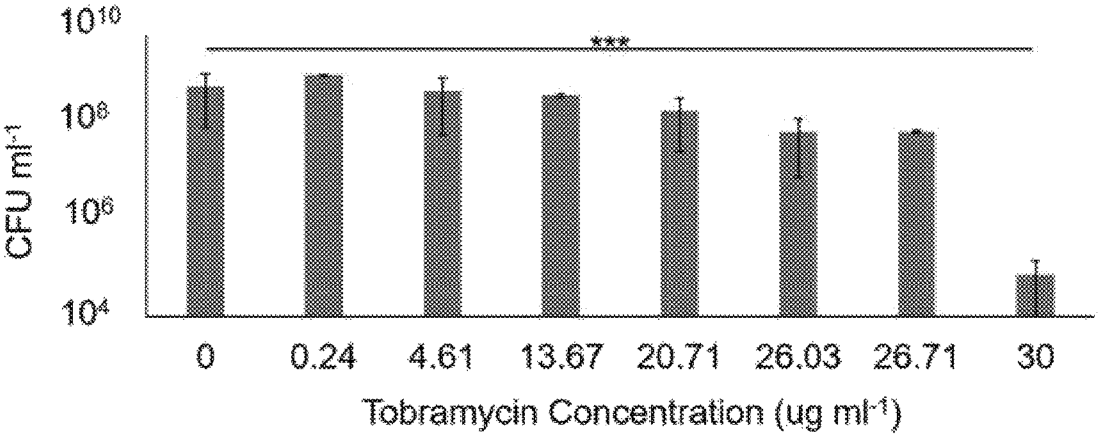
FIG. 21B shows the effect of the antibiotics against the biofilms in different concentrations from the eight outlets of the concentration gradient generator on colony formation units (CFU) at the second chamber, where the means and s.d. from triplicate experiments were shown. ***$P<0.001$.

Antimicrobial Testing and Cell-Cell Interaction Study Between Prokaryotic and Eukaryotic Cells In the foregoing example, in vitro human cell spheroid cultures or in vivo animal models had been incorporated into the present BDR microfluidic device to show that the BDR microfluidic device can be used to evaluate bacterial virulence. A rapid evaluation of antimicrobial susceptibility by biofilms is highly desired for identifying novel antibiofilm agents via high throughput screening of chemical libraries. Therefore, the BDR microfluidic device is also proposed for high-throughput cultivation and antimicrobial testing of biofilms. With an aid of the gradient generator, different concentrations of antibiotics can be generated against biofilms to evaluate their antimicrobial efficacy (FIGS. 21A and 21B).

Figure 22A:
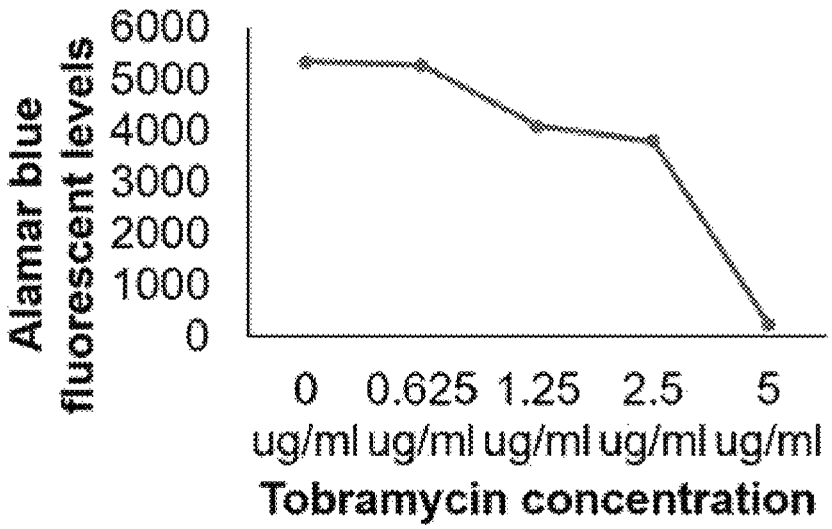
FIG. 22A shows the effect of antibiotics against biofilm in different concentrations on cell viability in terms of Alamar blue fluorescence.
Figure 22B:
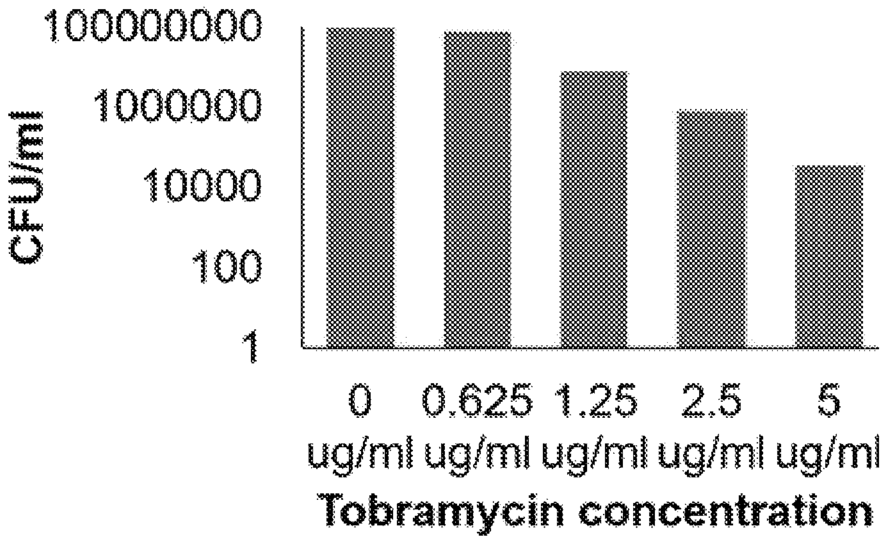
FIG. 22B shows the change in viable bacterial cell populations against an increasing concentration of the antibiotics.

Since Alamar blue is frequently used to evaluate the viability of eukaryotic and prokaryotic cells, this viability stain was used to evaluate the survival of static biofilms (without continuous flow) in the BDR microfluidic device after tobramycin treatment. FIG. 22A shows that the fluorescence level of Alamar blue decreased with increasing tobramycin treatment, which corroborated with the reducing bacterial numbers (FIG. 22B). These results indicate that dyes and stains could be flexibly incorporated into the BDR device for biosensing and survival detection purposes.

Figure 20:
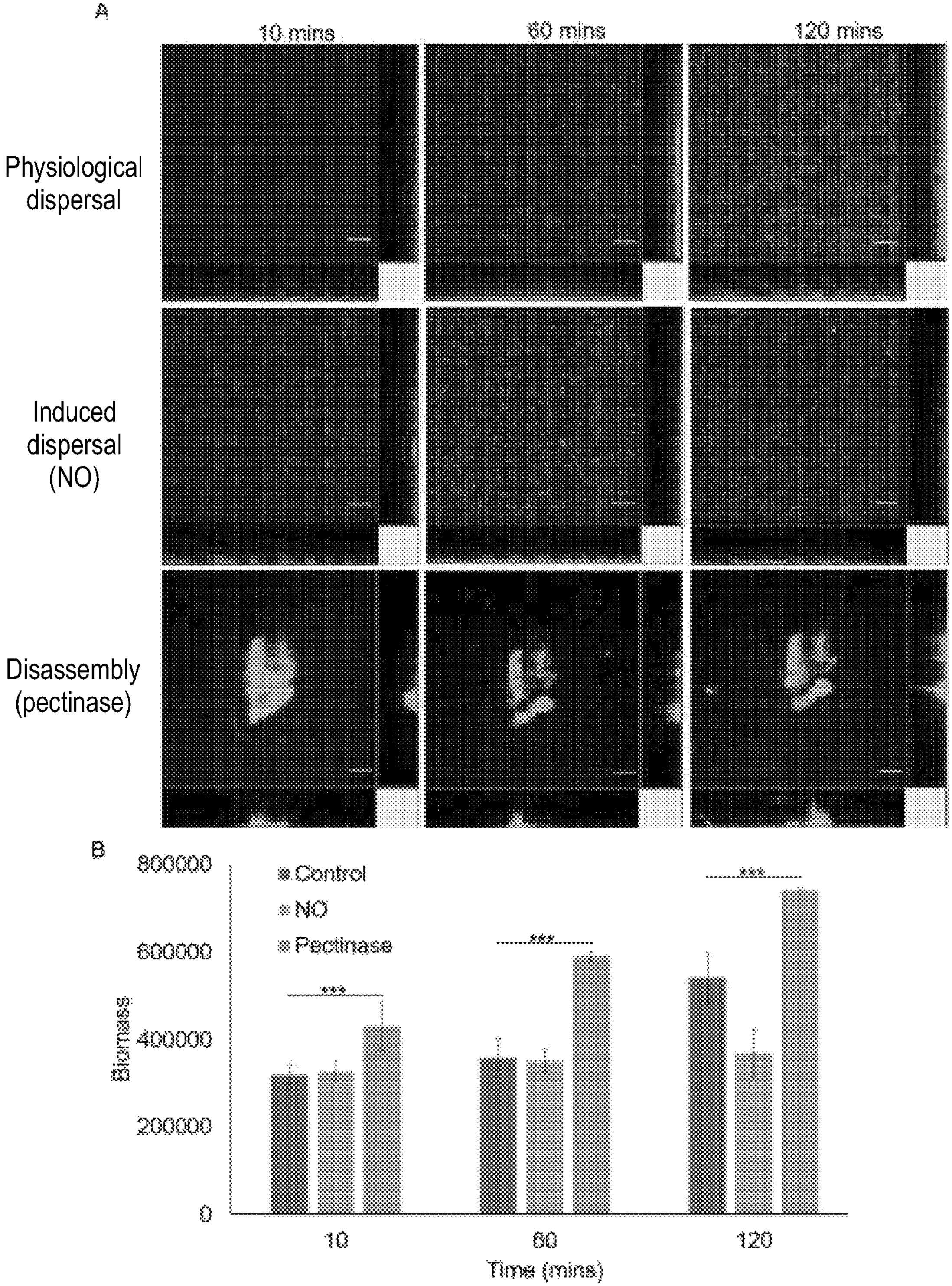
FIG. 20 shows (A) fluorescence images of CID- and EDA-released bacterial aggregates on human lung spheroids, where the scale bar is 10 μm; and (B) fluorescence intensity from CID-released and EDA-released GFP-tagged PAO1 on the human lung spheroids, where the means and s.d. from triplicate experiments were shown. ***$P<0.001$.

The proposed antibiofilm strategies adopting either biofilm dispersal or disassembly have varying implications for pathogenesis and disease dissemination. As biofilm-dispersed cells could not colonize on host surfaces, there were lower levels of the killing of eukaryotic hosts. Although this appeared to contradict with a previous work by the present inventors that CID cells possessed heightened virulence factors against the host macrophages upon direct exposure in a static infection model (Chua et al, 2014), the present disclosure demonstrates that CID-released bacteria could not colonize on the host and inflict virulence on the host, while EDA-released bacteria could colonize and kill the hosts more efficiently in continuous flow. It is possible that the larger EDA-released aggregates could settle downward onto the lung spheroids more efficiently than CID-released bacteria (FIG. 20), and the presence of flow could cause the unattached CID-released bacteria to be washed off from the lung spheroids, resulting in higher contact-based killing of lung spheroids by the EDA-released aggregates.

Figure 23A:
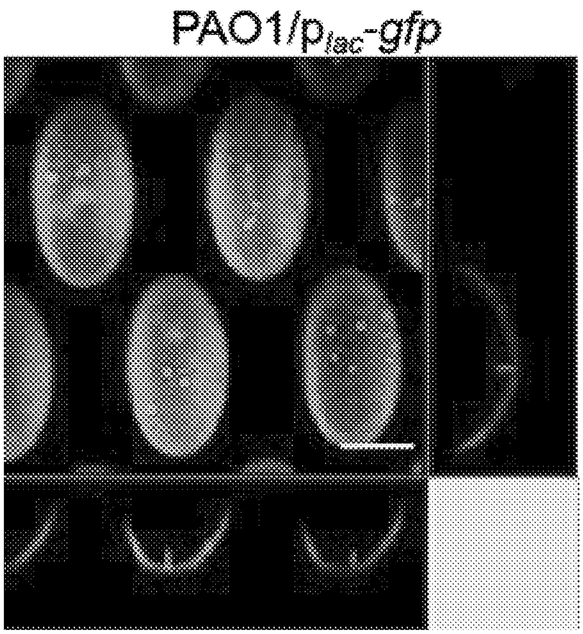
FIG. 23A shows fluorescence images of human monocytes (stained with SYTO-62 in red) attached on a biofilm of GFP-tagged wild-type *P. aeruginosa* (PAO1/$p_{lac}$-gfp), where the scale bar is 50 μm.
Figure 23B:
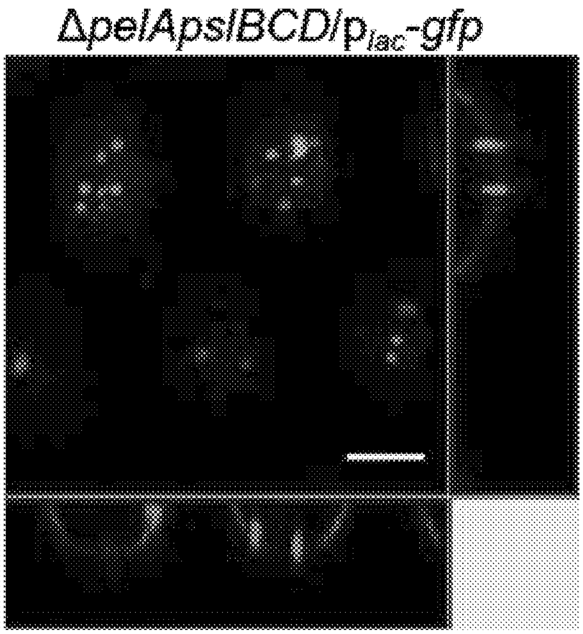
FIG. 23B shows fluorescence images of human monocytes introduced to a biofilm-deficient mutant of *P. aeruginosa* (ΔpelApslBCD), where the scale bar is 50 μm.

Besides evaluation of antimicrobial efficacy, the BDR microfluidic device could also be used to cultivate eukaryotic cells for studying eukaryotic-prokaryotic cell interactions. Human monocytes U937 were introduced into the biofilms and observed that they attached to the biofilms (FIG. 23A). In contract, when a biofilm-deficient mutant ΔpelApslBCD was used, minimal bacterial colonization and biofilm formation were observed, as the monocytes primarily attached to the microwell surface (FIG. 23B).

Compared to existing biofilm cultivation technologies, the present invention has at least the following advantages:

1. Evaluation of multicellular biofilms and disseminated cells under well-defined conditions over time.
2. Feasibility to assess drug efficacy, drug discovery, and design of therapeutic strategies.
3. Broad scope of application and relevance: the platform can be applied to different biological agents, including prokaryotic and eukaryotic biofilms.
4. Ease of operation: Operators can easily use the platform with minimal training (for syringe pumps).
5. High throughput: Through multiplexing of the device, the primary prototype can access 32 sample conditions in parallel. With appropriate settings (such as having an external casing), a greater degree of multiplexing can be achieved (up to 96 samples per run).
6. Ease of observation: the device is transparent, so observing biofilms with a microscope is convenient.

Table 2 below summarizes the differences between some conventional techniques and the present BRD microfluidic device

TABLE 2

| Type | Biofilm life cycle stage | Media supply | Time | Cost | Throughput | Reference |
|---|---|---|---|---|---|---|
| Colony on agar plate | Growth | Static (15-25 ml per plate) | 1-3 days | Low | Medium | (1, 2) |
| Coupon/glass slides | Colonization + Growth | Static (10-20 ml) | 1-3 days | Low | Medium | (3, 4) |
| Calgary biofilm device | Colonization + Growth | Static (200 μl per well) | 1-3 days | Low | High | (5) |
| Flow chamber | Colonization + Growth | Continuous (1 L per channel) | 3-5 days | Mid | Low | (6) |

TABLE 2-continued

| Type | Biofilm life cycle stage | Media supply | Time | Cost | Throughput | Reference |
|---|---|---|---|---|---|---|
| Bioreactor | Colonization + Growth | Static/ continuous (1 L-10 L) | Weeks-months | High | Low | (7) |
| BDR platform | Growth + Dispersion + Recolonization+ Infection | Continuous (50 ml) | 6-12 hrs | Low | High | Present Invention |

A more detailed comparison between the present invention and two conventional biofilm culture models is summarized in Table 3 below.

TABLE 3

| | Traditional 2D culture, grown on peg lids or wells | Flow chamber model | Present invention |
|---|---|---|---|
| Cultivation duration | 24-48 hrs | At least 72 hrs | 6-12 hrs |
| Media flow | None (Static, with limited nutrients) | Continuous, with continual nutrient replenishment and waste removal | Continuous, with continual nutrient replenishment and waste removal |
| Potential for high-Throughput | Variable (low for Petri dishes and high for 96-well microwell plates | Low (3 channels) | Medium (8 channels) |
| Real-time monitoring using microscope | No | Yes | Yes |
| 2D/3D model | 2D (flat surface) | 2D (flat surface) | 3D |
| Observation of Biofilm life cycle | Biofilm formation | Biofilm colonization and formation | Biofilm colonization, formation, dispersal and recolonization of fresh areas |

Materials and Methods

Bacterial Strains and Growth Conditions

The bacterial strains used in the present disclosure are listed in Table 4. *E. coli* DH5a strain was used for standard DNA manipulations. LB medium (Difco. Becton Dickinson and Company, USA) was used to cultivate *E. coli*, and *P. aeruginosa* strains for bacterial growth. For certain experiments, *P. aeruginosa* strains were grown in ABTGC (ABT minimal medium supplemented with 2 g $L^{-1}$ glucose and 2 g $L^{-1}$ casamino acids at 37° C. (35). For plasmid maintenance in *E. coli*, the medium was supplemented with 100 μg $ml^{-1}$ ampicillin and 15 μg $ml^{-1}$ gentamicin. For marker selection in *P. aeruginosa,* 30 μg $ml^{-1}$ gentamicin and 100 μg $ml^{-1}$ streptomycin were used.

TABLE 4

| Strain | Description | Source/ Reference |
|---|---|---|
| | *P. aeruginosa* | |
| PAO1 | Prototypic nonmucoid wild-type strain | Li et al., 2014 |
| PAO1/$p_{lac}$-gfp | Strep$^r$, PAO1 containing the Tn7-transposon ($p_{lac}$-gfp), with constitutively expressed GFP | Barraud et al., 2006 |

TABLE 4-continued

| Strain | Description | Source/ Reference |
|---|---|---|
| ΔpelA/$p_{lac}$-gfp | Strep$^r$, Pel defective pelA mutant in PAO1, containing the Tn7-transposon ($p_{lac}$-gfp), with constitutively expressed GFP. | Rumbaugh and Sauer, 2020 |
| ΔpslBCD/$p_{lac}$-gfp | Strep$^r$, Psl defective pelBCD mutant in PAO1, containing the Tn7-transposon ($p_{lac}$-gfp), with constitutively expressed GFP. | Rumbaugh and Sauer, 2020 |
| ΔpelAΔpslBCD/$p_{lac}$-gfp | Strep$^r$, Pel and Psl exopolysaccharides defective pelA and pslBCD mutant in PAO1, containing the Tn7-transposon ($p_{lac}$-gfp), with constitutively expressed GFP. | Rumbaugh and Sauer, 2020 |
| PAO1/$p_{BAD}$-yhjH | PAO1 containing the $p_{BAD}$-yhjH vector | Yu and Chua, 2020 |
| PAO1/$p_{BAD}$-yhjH/$p_{lac}$-gfp | Strep$^r$; PAO1 containing the $p_{BAD}$-yhjH vector and the Tn7-transposon ($p_{lac}$-gfp), with constitutively expressed GFP | Present Invention |
| PAO1/$p_{cdrA}$-gfp | Carb$^r$, PAO1 carrying the c-di-GMP reporter plasmid. | Guilhen et al., 2017 |
| ΔbdlA/$p_{lac}$-gfp | Strep$^r$; ΔbdlA mutant containing the Tn7-transposon ($p_{lac}$-gfp), with constitutively expressed GFP. | Present Invention |
| ΔbdlA/$p_{lac}$-bdlA/$p_{lac}$-gfp | Gm$^r$; Strep$^r$; ΔbdlA mutant containing the $p_{lac}$-bdlA pUCp complementation plasmid and Tn7-transposon ($p_{lac}$-gfp), with constitutively expressed GFP. | Present Invention |
| ΔfliM/$p_{lac}$-gfp | Strep$^r$; flagella mutant containing the Tn7-transposon ($p_{lac}$-gfp), with constitutively expressed GFP. | Present Invention |
| ΔfliM/$p_{lac}$-fliM /$p_{lac}$-gfp | Gm$^r$; Strep$^r$; ΔfliM mutant containing the $p_{lac}$-fliM pUCp complementation plasmid and Tn7-transposon ($p_{lac}$-gfp), with constitutively expressed GFP. | Present Invention |
| ΔpelA/ p $_{lac}$-yedQ | GM$^r$; ΔpelA carrying the pYedQ vector | Rumbaugh and Sauer, 2020 |
| PA14/$p_{lac}$-gfp | Strep$^r$, containing the Tn7-transposon ($p_{lac}$-gfp), with constitutively expressed GFP | Present Invention |
| PA23376/$p_{lac}$-gfp | Strep$^r$ containing the Tn7-transposon ($p_{lac}$-gfp), with constitutively expressed GFP | Present Invention |
| PA14476/$p_{lac}$-gfp | Strep$^r$, containing the Tn7-transposon ($p_{lac}$-gfp), with constitutively expressed GFP | Present Invention |
| | *E. coli* | |
| DH5a | $F^-$, ø80dlacZΔM15, Δ(lacZYA-argF)U169, deoR, recA1, endA1, hsdR17($rK^-$, $mK^+$), phoA, supE44, λ–, thi-1, gyrA96, relA1 | Laboratory collection |

Fabrication of Device

Using standard fabrication methods, the CAD software designed the microfluidic device as four components. The master mold was fabricated by diffuser back-side lithography procedures. The base layer was composed of an array of 300 microwells each with a dimension of 150×250×150 μm (length×width×depth). The second 8-channel layer comprised the primary chamber and serpentine secondary chamber, each with a 6 mm depth separated by a valve. The third layer comprised a tree-shaped gradient generator composed of two inlet channels and eight output channels. The material for fabrication of the microfluidic device was polydimethylsiloxane (PDMS), which was prepared using a Sylgard 184 silicone elastomer kit (Dow Corning, USA) by thoroughly mixing the base resin and curing agent in a ratio of 10:1 by weight. The cured PDMS molds were plasma treated and exposed to trichloro(1H,1H,2H,2H-perfluorooctyl) silane (Sigma-Aldrich, #448931, Germany) overnight in a vacuum desiccator. The different layers were bonded together using plasma technology and placed in a 70° C. oven for 2 hours.

Calibration of the Gradient Generator

The device was primed with ethanol and checked to ensure no trapped air bubbles. The ddH2O and 10 μM SYTO-9 fluorescent dye (Invitrogen. USA) were pumped into the gradient generator at 30 μl $min^{-1}$ through both inlets separately with a syringe pump (New Era Pump Systems. Farmingdale, USA). Liquid samples were collected from each outlet for fluorescence density measurement with a microplate reader (Tecan, Infinite M1000 Pro, Switzerland). To visualize the gradient distribution generated in the device, blue and red food dyes were introduced separately into both inlets with the syringe pump. The simulated flow profile was generated using the multiphysics modelling software (COMSOL) (FIG. 2B).

Cultivation of Biofilms in Device

*P. aeruginosa* biofilms were cultivated in an ABTGC medium at 37° C. The device was supplied with a medium flow using the syringe pump, while the waste medium was removed into a waste beaker. Each channel was inoculated with 100 μl of a 100× diluted overnight culture using a syringe and needle, followed by incubation without flow for 20 mins to allow bacteria to colonize the microwells. Medium flow was started for continuous flow and maintained at a velocity of 0.2 mm/s by the syringe pump (New Era Pump Systems, Farmingdale, USA) for 12 hrs at 37° C.

Biofilm Induced Dispersal (CID) and Enzymatic Disassembly (EDA)

The device comprises primary and secondary chambers. The primary chamber was used for biofilm cultivation and subsequent dispersal, and the secondary chamber filled with only media was left isolated via a closed valve. For biofilm dispersal and disassembly, the valve was opened to connect both chambers, enabling the movement of bacteria from the primary to the secondary chamber.

During induced biofilm dispersal (CID), the 150 μM sodium nitroprusside dihydrate (SNP, Sigma-Aldrich, Germany) was used for *P. aeruginosa* wild-type PAO1 strain, while 5% (w/v) L-arabinose (Sigma-Aldrich, Germany) was used for PAO1/$p_{BAD}$-yhjH strain. For biofilm disassembly. the 100 units/ml cellulase (from *Trichoderma reesei*, Sigma-Aldrich, Germany) and 12.5 units/ml pectinase (from *Aspergillus aculeatus*, Sigma-Aldrich, Germany) were employed as biofilm disrupting agents. The chemicals were flowed into the device by the syringe pump at a constant speed for 2 hrs at 37° C. Biofilm-released bacterial cells were collected from the waste outlet for further analysis.

Microscopic Image or Video Acquisition of Biofilms

All microscopic images of biofilms and dispersed cells were captured by a Leica TCS SP8 MP Multiphoton/Confocal Microscope system using a 10× objective and secondary lens zoom of 40× to monitor brightfield and GFP fluorescence in Z-stacks. For closer observation of biofilm-released PAO1/$p_{cdrA}$-gfp cells, these cells were collected from the device and direct observed using the Leica TCS SP8 MP Multiphoton/Confocal Microscope system with a 63× objective. ImageJ, LAS X, and Imaris software (Bitplane AG, Zurich, Switzerland) were used to process the images. The formula used to quantify GFP fluorescence levels was corrected total cell fluorescence (CTCF)=integrated density−(area of selected cells×mean fluorescence of background readings).

Bacterial Biofilm Video Capturing

Time-lapse photography was performed using the biofilm tracking function in Imaris software and ImageJ according to the manufacturer's instructions. Cell movement trajectories and associated data such as average fluorescent intensities and average velocities were exported for analysis.

Mathematical Modelling

Mathematical modelling of the bacterial fluorescence signals comprises video processing using a Python program and data processing using MATLAB. The modelling program can be divided into two parts: 1. video processing and 2. data processing. During video processing, the program grayscales the photo, and then counts all the pixels with brightness. Most of the background noise was at 0~30, while FIG. 10A showed that most of the fluorescence signal was within range of 60~90.

For data processing, the program will count the number of white pixels in each image and save the value into a txt file. The program would normalize the starting value to the same intensity during data processing and use cftool in MATLAB to fit data. The regression formulas used by MATLAB are polynomial and exponential regression, as follows.

First-Order Polynomial Regression:

$$y = ax + b \quad (1)$$

Second-Order Polynomial Regression:

$$y = ax^2 + bx + c \quad (2)$$

Fourth-Order Polynomial Regression:

$$y = ax^4 + bx^3 + cx^2 + dx + e \quad (3)$$

Exponential Regression:

$$y = a \cdot e^{bx} \quad (4)$$

where a, b, c, d and e are the parameter that needs to be fitted. x is the number of each frame in video, y is the intensity after normalization.

The $R^2$ is a value to measure how well a model can predict the data. The higher the value of $R^2$ is, the better is the model at predicting the data. The value of $R^2$ can be calculated as the equation below:

$$R^2 = 1 - \frac{\sum_{i=1}^{n}(y_i - \hat{y}_i)^2}{\sum_{i=1}^{n}(y_i - \bar{y})^2} \quad (5)$$

where $\hat{y}$ the calculated values of regression equation, $\bar{y}$ is the mean value of y.

Quantification of Bacterial Numbers by Colony-Forming Units (CFU)

Biofilm-released bacteria were collected directly from the waste outlet of the secondary chamber. 1 ml of 0.9% NaCl (w/v) saline was flushed repeatedly into each chamber to dislodge the biofilms to retrieve biofilm bacteria from primary and secondary chambers. Biofilm cells were then homogenized by sound sonication (Elmasonic P120H, power=50%, frequency=37 KHz) in an ice-cold water bath for 15 mins, followed by vigorous vortexing for 5 mins. As previously described (19), cell suspensions were serially diluted in saline and transferred to LB agar plates (5 replicates) for incubation for 16 hrs at 37° C. Colonies were enumerated, where the CFU/ml is tabulated by (colony number×dilution factor)/volume.

Quantification of c-Di-GMP Levels in Bacterial Biofilms by ELISA

Bacterial samples were collected and then sonicated at 40% amplitude for 5 min through a sonicate machine (SFX 550, SSE-1, Branson, Emerson, USA) with 45 sec on/60 sec off output to lyse bacteria. The c-di-GMP concentration was tested by a c-di-GMP ELISA kit (LMAI, Shanghai, China) according to the manufacturer's protocol and measured at OD490 by a microplate reader (Tecan, Infinite M1000 Pro, Switzerland).

Isolation and Quantification of Exopolysaccharide Concentration

Psl was extracted by growing ΔpelA/$p_{lac}$-YedQ static biofilms on standard Petri dishes containing 15 ml LB supplemented with appropriate antibiotics at 37° C. for 16 hrs. The biofilms were centrifuged for separation from the supernatant at 10,000 g for 5 mins. The cell pellet was resuspended in 5 ml of 0.9% NaCl and subjected to mild water-bath sonication (Elmasonic P120H, power=50%, frequency=37 kHz, 5 min) to separate the cells from the surface-associated matrix. Centrifugation separated the cells from the matrix, leaving the crude matrix extract behind in the supernatant. The crude extract was then further treated by removing eDNA by precipitation with 25% ethanol and 0.1 M $CaCl_2$, followed by degradation of extracellular proteins by 0.5 mg $ml^{-1}$ Proteinase K at 60° C. for 1 hr and inactivation at 80° C. for 30 mins. The crude extract was then filtered with a centrifugal filter (<3 kDa) to remove the metabolites. The extract was then lyophilized and resuspended in sterile $ddH_2O$. The polysaccharide concentration was determined by the phenol-sulfuric acid colorimetric method (57).

Biofilm Disruption Assay in 24 Wells Plate

Bacteria were cultivated in 1 ml ABTGC medium in each well of a 24-well cell culture plate (SPL Life Science Co., Ltd) at 37° C. for 12 hrs for biofilm formation. The biofilms were washed trice with 0.9% NaCl to remove planktonic bacteria, followed by pectinase treatment at various concentrations in an ABTGC medium. After further incubation at 37° C. for 12 hrs, the biofilms were washed three times with 0.9% NaCl, scraped from the well surface with a cell scraper, and resuspended in 1 ml 0.9% NaCl for CFU assay.

Exogenous Addition and Coating of Exopolysaccharides on Microwells

The Pel and Psl exopolysaccharides were extracted as described previously (42). The extracted 10 ug $ml^{-1}$ Pel or Psl were evenly coated on the surface of the microwells at 4° C. for 16 hrs and dried. The ΔpelAΔpslBCD/$p_{lac}$-gfp biofilm was then cultivated on the microwells coated with Pel or Psl for further analysis.

Cultivation of Human Lung Fibroblasts and 3D Spheroids

Human lung fibroblasts (ATCC PCS-201-013, HLF) were cultivated in Dulbecco's Modified Eagle Medium (DMEM, Gibco, USA) supplemented with 10% fetal bovine serum (FBS, Gibco, USA) at a density of $1.0\times10^6$ cells $ml^{-1}$ in a T25 flask (SPL, Korea) at 37° C., 5% $CO_2$, 99% humidity for 72 hrs. For the generation of 3D spheroids as previously described (58), the cell droplets (20 μl) were placed on the lid of a hydrated 60×15 mm cell culture dish and incubated at 37° C., 5% $CO_2$, 99% humidity for 24 hrs. The spheroids were transferred into the secondary chamber of the BDR platform using a sterile syringe and needle, followed by incubation at 37° C., 5% $CO_2$, and 99% humidity for 20 mins to enable attachment to the bottom of microwells.

Infection of Human Lune Spheroids by Biofilm-Released Bacteria

After the biofilm growth and bacteria dispersion in the primary chamber, the gfp-tagged bacterial cells were introduced into the secondary chamber containing the lung spheroids at a flow rate of 4 ml $hr^{-1}$. The infection was established at 37° C., 5% $CO_2$, 99% humidity for 0 hr, 2 hrs and 5 hrs. Lung spheroids were stained with 3 μm CellTracker Deep Red Fluorescent Stain (Invitrogen, USA) and Propidium Iodide (PI, Invitrogen, USA) to observe the infection directly using the confocal microscope (Leica TCS SP8 MP) with a 40× objective. ImageJ, LAS X, and Imaris software (Bitplane AG, Zurich, Switzerland) were used to process the images. The fluorescence intensities of Deep Red and PI were measured using ImageJ. The PI fluorescence/CellTracker deep-red fluorescence ratio×100% was quantified to tabulate the percentage of dead cells in the lung spheroids.

Cultivation of *C. elegans*

As previously described (42), the *E. coli* OP50 strain was prepared as nematode feed by growing the bacterial lawn on Nematode growth medium (NGM) agar plates at 37° C. for 16 hrs. The *C. elegans* N2 strain was cultivated on an OP50 lawn at room temperature for 72 hrs to expand the population.

Cultivation and Infection of *C. elegans* in the BDR Platform

Prior to the experiment, the L3 stage animals were introduced into the secondary chamber of the BDR platform with syringe injection, where at least one worm was introduced into each microwell of the channels. After biofilm growth and bacteria dispersion in the primary chamber, the gfp-tagged bacterial cells were flown into the secondary chamber containing the lung spheroids at a flow rate of 4 ml $hr^{-1}$. The infection was established at 37° C., 5% $CO_2$, 99% humidity for 0 hrs, 3 hrs, 6 hrs and 12 hrs. The number of live (moving) and dead (non-motile) nematodes from the microwells were observed and tabulated under a stereomicroscope (Zeiss). For imaging, the *C. elegans*-biofilm model was observed using the confocal microscope (Leica TCS SP8 MP) with a 40× objective.

The live nematodes were collected from the secondary chamber and washed 3 times with 0.9% NaCl to quantify the PAO1 numbers in the animals. The animals were then ground by the microtube pellet pestle (Sigma-Aldrich, Germany) for release of bacteria and resuspension in 1 ml 0.9%

NaCl. The bacterial suspension was serially diluted in 0.9% NaCl and plated on *Pseudomonas* isolation agar (PIA) for CFU assay.

Alamar-Blue Quantification

The PAO1 culture was diluted 100-fold in ABTGC media and inoculated at 100 μl into each channel of the microfluidic model using a syringe and needle. Then the model was placed in a 37° C. incubator for 20 mins to allow bacteria to colonize the bottom of the microwells. ABTGC media containing tobramycin (Sigma) with concentrations of 0, 0.625, 1.25, 2.5, 5 ug/ml were injected into each chamber for 12 hrs treatment. Alamar blue cell viability reagent (Thermo Fisher) was diluted with culture media to 10% and injected into chambers, then incubated at 37° C. until the color changed from blue to pink. The colored liquid was collected from the chamber for direct measurement of OD600 nm and fluorescence (Ex: 560 nm, Em: 590 nm) using a microplate reader (Thermo Scientific Varioskan LUX Multimode Microplate Reader).

Monocyte-Biofilm Coculture Model

The human monocytic cell line U937 was cultured in RPMI 1640 medium containing 10% FBS, penicillin (50 U/ml), and streptomycin (100 μg/ml) at 37° C. in a 5% $CO_2$ and 99% humidity. For the experiment, monocytes number were first adjusted to $1\times10^3$ cells $ml^{-1}$ and stained with 5 μM SYTO™ 62 Red Fluorescent Nucleic Acid Stain (Invitrogen, USA) for 10 mins, followed by introduction into the BDR device containing *P. aeruginosa* biofilms using a syringe pump (New Era Pump Systems, Farmingdale, USA) at 4 ml $hr^{-1}$ to make sure there are 3-5 cells in every microwell. The Z-stack images were captured using a Leica TCS SP8 MP Multiphoton/Confocal Microscope system (10× objective and secondary lens zoom of 20×) to monitor brightfield, GFP (Ex: 495 nm; Em: 545 nm), and SYTO 62 (Ex: 638 nm; Em: 680 nm) fluorescence. IMARIS (Bitplane, Switzerland was used to process the images.

Statistical Analysis

The results were expressed as means±standard deviation. Data groups were analyzed using the one-way ANOVA and Student's t-test to evaluate associations between independent variables, and the p values were calculated. Three independent trials were conducted in triplicates for each experiment, where the results were shown as the mean±standard deviation Although the invention has been described in terms of certain embodiments, other embodiments apparent to those of ordinary skill in the art are also within the scope of this invention. Accordingly, the scope of the invention is intended to be defined only by the claims which follow.

INDUSTRIAL APPLICABILITY

Potential applications of the present invention include:

1. Cultivation of any biological agents and analysis of the dissemination of biological agents;
2. Treatment of biological agents using compound screening, validation, and combinatorial treatment;
3. Multiplexing devices for high throughput screening of chemical and biological agents on biological agents.

What is claimed is:

1. An integrated system for multiple cultivations of a biological agent, formation of a culture model, and evaluation of an efficacy of a test agent on dispersing or disassembling the culture model, the integrated system being a microfluidics, the microfluidics comprising:

at least two separate chambers configured for a primary cultivation of the biological agent, formation of the culture model, and a secondary cultivation of the biological agent released from the culture model;

a fluid flow control mechanism to control fluid communication comprising a flow of the biological agent between two of the at least two separate chambers; and a gradient generator comprising at least two fluid inlets and a plurality of fluid outlets for introduction of a concentration gradient of an analyte to the culture model in one of the at least two separate chambers, wherein each of the at least two separate chambers comprises a plurality of microwells each comprising a cell culture surface configured to facilitate the formation of the culture model thereon.

2. The integrated system of claim 1, wherein a first chamber of the at least two separate chambers is disposed upstream to a second chamber of the at least two separate chambers, wherein the first chamber comprises a first plurality of microwells and the second chamber comprises a second plurality of microwells, wherein each of the first plurality of microwells or each of the second plurality of microwells comprises the cell culture surface configured to facilitate the formation of the culture models.

3. The integrated system of claim 2, wherein the cell culture surface comprises a plurality of micropores.

4. The integrated system of claim 2, wherein the cell culture surface is coated with a layer of material to facilitate the formation of the culture models.

5. The integrated system of claim 2, wherein the first plurality of microwells and the second plurality of microwells are tapered microwells.

6. The integrated system of claim 1, wherein the biological agent comprises prokaryotic cells, eukaryotic cells or tissues, or any combination thereof.

7. The integrated system of claim 1, wherein the culture model is a three-dimensional multicellular structure comprising microbial biofilms and/or mammalian cell spheroids.

8. The integrated system of claim 7, wherein the microbial biofilms comprise bacterial biofilms comprising biofilms formed by *Pseudomonas aeruginosa* or any mutant thereof.

9. The integrated system of claim 2, wherein the fluid flow control mechanism is a valve to control the fluid communication between the first chamber and the second chamber.

10. The integrated system of claim 1, wherein the test agent comprises chemical substance, biological cell or tissues, or a combination thereof.

11. A method for fabricating the integrated system of claim 1, the method comprising:

providing a first layer of the microfluidics comprising an array of microwells disposed in two separate regions corresponding to a first chamber and a second chamber of the at least two chambers for a primary cultivation and a secondary cultivation of a biological agent and formation of a culture model;

providing a second layer disposed on the first layer of the microfluidics comprising multiple fluid channels and the fluid flow control mechanism to separate the fluid channels in the first chamber from those in the second chamber, wherein the first chamber is disposed upstream to the second chamber;

providing a third layer disposed on the second layer of the microfluidics comprising the gradient generator for introducing a concentration gradient of the test agent to the culture model in the first chamber, wherein the gradient generator is disposed upstream to the first chamber; and aligning and bonding the first layer, the second layer and the third layer in an order from the bottom to the top of the integrated system.

12. The method of claim 11, wherein the microwells are tapered microwells and an interior surface thereof is modified to facilitate the formation of the culture model from the biological agent introduced to the first chamber and any biological agent released from the culture model in the first chamber to the second chamber.

13. The method of claim 12, wherein the interior surface of the microwells comprises a plurality of micropores or a layer of coating to facilitate the formation of the culture models.

14. The method of claim 12, wherein each of the tapered microwells has a dimension of 150×250×150 μm for length, width and depth of the tapered microwells, respectively.

15. The method of claim 11, wherein the first chamber and the second chamber each has a channel depth of 6 mm.

16. The method of claim 11, wherein the gradient generator comprises at least two fluid inlets for mixing two substances to form the test agent and a plurality of fluid outlets for generating the concentration gradient of the test agent before introduction to the first chamber.

17. The method of claim 11, wherein the microfluidics is made of polydimethylsiloxane.

18. A method for characterizing an anti-microbial in terms of eliminating a biofilm under a chemical-induced dispersal or enzymatic disassembly mechanism, the method comprising:

providing a biological agent to a first chamber of the microfluidics of the integrated system according to claim 2 in which a primary cultivation of the biological agent and formation of a culture model will take place while the fluid communication between the first chamber and a second chamber being blocked by the fluid flow control mechanism;

providing the anti-microbial to the first chamber of the microfluidics;

contacting the anti-microbial with the culture model in the first chamber while the fluid communication between the first chamber and the second chamber being unblocked by the fluid flow control mechanism; and observing any cellular, molecular, genetic, morphological, chemical and/or behavioral changes of the biological agent released from the culture model in the first chamber to the second chamber in which a recolonization and a secondary cultivation of the biological agent may take place, wherein the biological agent is a biofilm-forming microbe under a culture condition, and if no recolonization or formation of the culture model is observed in the second chamber, the anti-microbial is a biofilm chemical-induced dispersal agent; otherwise, the anti-microbial is a biofilm enzymatic disassembly agent.

19. A method for determining an efficacy of an anti-microbial to eliminate a biofilm comprising:

providing a biological agent to a first chamber of the microfluidics of the integrated system according to claim 2 in which a primary cultivation of the biological agent and formation of a culture model will take place while the fluid communication between the first chamber and a second chamber being blocked by the fluid flow control mechanism;

providing the anti-microbial to the gradient generator of the integrated system;

contacting the anti-microbial with the culture model in the first chamber while the fluid communication between the first chamber and the second chamber being unblocked by the fluid flow control mechanism; and quantifying any cellular, molecular, genetic, morphological, chemical and/or behavioral changes in the biological agent against a concentration gradient of the anti-microbial in order to determine the efficacy of the anti-microbial to eliminate the biofilm.

20. A method for studying cell-cell interaction comprising:

providing a first biological agent to a first chamber of the microfluidics of the integrated system according to claim 2 in which a primary cultivation of the biological agent and formation of a culture model will take place while the fluid communication between the first chamber and a second chamber being blocked by the fluid flow control mechanism;

providing a second biological agent to the first chamber of the microfluidics;

contacting the second biological agent with the culture model while the fluid communication between the first chamber and the second chamber being unblocked by the fluid flow control mechanism; and observing any cellular, molecular, genetic, morphological, chemical and/or behavioral changes of the first biological agent released from the culture model in the first chamber to the second chamber in which a recolonization and a secondary cultivation of the biological agent may take place, and any cellular, molecular, genetic, morphological, chemical and/or behavioral changes of the second biological agent, wherein the first biological agent is a different species of organisms, type of cells or tissues from the second biological agent.

* * * * *